US010266547B2

(12) United States Patent
Caldarelli et al.

(10) Patent No.: US 10,266,547 B2
(45) Date of Patent: *Apr. 23, 2019

(54) THIENO[2,3-E]INDOLE DERIVATIVES AS NEW ANTITUMOR AGENTS

(71) Applicant: NERVIANO MEDICAL SCIENCES S.R.L., Nerviano (IT)

(72) Inventors: Marina Caldarelli, Milan (IT); Michele Caruso, Milan (IT); Paolo Orsini, Legnano (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,746

(22) PCT Filed: Sep. 16, 2014

(86) PCT No.: PCT/EP2014/069681
§ 371 (c)(1),
(2) Date: Mar. 22, 2016

(87) PCT Pub. No.: WO2015/044003
PCT Pub. Date: Apr. 2, 2015

(65) Prior Publication Data
US 2016/0229867 A1    Aug. 11, 2016

(30) Foreign Application Priority Data

Sep. 25, 2013  (EP) .................................. 13185935

(51) Int. Cl.
| | | |
|---|---|---|
| A61K 31/27 | (2006.01) | |
| A61K 31/4015 | (2006.01) | |
| A61K 31/407 | (2006.01) | |
| A61K 38/06 | (2006.01) | |
| A61K 45/06 | (2006.01) | |
| C07D 495/04 | (2006.01) | |
| C07K 5/097 | (2006.01) | |

(52) U.S. Cl.
CPC ............ *C07D 495/04* (2013.01); *A61K 31/27* (2013.01); *A61K 31/407* (2013.01); *A61K 31/4015* (2013.01); *A61K 38/06* (2013.01); *A61K 45/06* (2013.01); *C07K 5/0821* (2013.01)

(58) Field of Classification Search
CPC combination set(s) only.
See application file for complete search history.

(56) References Cited

U.S. PATENT DOCUMENTS 9,527,863 B2 * 12/2016 Beria .................... C07D 495/04
9,561,290 B2 *  2/2017 Beria .................... C07D 495/04

FOREIGN PATENT DOCUMENTS

| | | | |
|---|---|---|---|
| GB | 2 344 818 A | 6/2000 | |
| WO | WO 02/083180 A1 | 10/2002 | |
| WO | WO 2004/043493 A1 | 5/2004 | |
| WO | WO 2005/079398 A2 | 9/2005 | |
| WO | WO 2005/105154 A1 | 11/2005 | |
| WO | WO 2006/012527 A1 | 2/2006 | |
| WO | WO 2010/009124 A2 | 1/2010 | |
| WO | WO 2013/149946 A1 | * 10/2013 | |
| WO | WO 2013/149948 A1 | * 10/2013 | |

OTHER PUBLICATIONS

Tichenor et al. "Rational Design, Synthesis, and Evaluation of Key Analogues of CC-1065 and the Duocarmycins" J. Am. Chem. Soc. 2007, 129, 14092-14099.*
U.S. Appl. No. 15/359,703, filed Mar. 2013, Beria et al.*
Baird R. et al., "Neighboring Carbon and Hydrogen. LI. Dienones from Arlo-3 Participation. Isolation and Behavior of Spiro(2,5)Octa-1,4-Diene-3-One", J. Am. Chem. Soc. 85:567-578 (Mar. 5, 1963).
Boger D.L. et al., "Enantioselective Total Synthesis of (+)-Duocarmycin A, epi-(+)-Duocarmycin A, and Their Unnatural Enantiomers", J. Am. Chem. Soc. 118(9):2301-2302 (1996).
Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Greenwald R.B. et al., "Effective Drug Delivery by PEGylated Drug Conjugates", Advanced Drug Delivery Reviews 55:217-250 (2003).
Jeffrey S.C. et al., "Design, Synthesis, and In Vitro Evaluation of Dipeptide-Based Antibody Minor Groove Binder Conjugates", Journal of Medicinal Chemistry 48(5):1344-1358 (2005).
Kingsbury W.D. et al., "A Novel Peptide Delivery System Involving Peptidase Activated Prodrugs as Antimicrobial Agents. Synthesis and Biological Activity of Peptidyl Derivatives of 5-Fluorouracil", Journal of Medicinal Chemistry 27(11):1447-1451 (1984).
Nagamura S. et al., "Synthesis and Antitumor Activity of Duocarmycin Derivatives: A-Ring Pyrrole Analogues of Duocarmycin B2", Bioorganic & Medicinal Chemistry 4(8):1379-1391 (1996).
Tichenor M.S. et al., "Rational Design, Synthesis, and Evaluation of Key Analogues of CC-1065 and the Duocarmycins", J. Am. Chem. Soc. 129:14092-14099 (2007).
Toki B.E. et al., "Protease-Mediated Fragmentation of p-Amidobenzyl Ethers: A New Strategy for the Activation of Anticancer Prodrugs", J. Org. Chem. 67(6):1866-1872 (2002).

(Continued)

*Primary Examiner* — Amanda L Aguirre
(74) *Attorney, Agent, or Firm* — Scully, Scott, Murphy & Presser, P.C.

(57) ABSTRACT

The present invention relates to a novel class of alkylating agents comprising a thieno[2,3-e]indole moiety tethered to a DNA-binding moiety, which have cytotoxic activity and are useful in treating diseases such as cancer, cellular proliferation disorders and viral infections. The present invention also provides methods for preparing these compounds, pharmaceutical compositions comprising them and methods of treating diseases utilizing such compounds or the pharmaceutical composition containing them. The invention also relates to the use of this novel class of alkylating agents in the preparation of conjugates.

9 Claims, 5 Drawing Sheets

(56) References Cited

OTHER PUBLICATIONS

Tranoy-Opalinski I. et al., "Design of Self-Immolative Linkers for Tumour-Activated Prodrug Therapy", Anti-Cancer Agents in Medicinal Chemistry 8(6):618-637 (2008).
Wang Y. et al., "CC-1065 Analogues Bearing Different DNA-Binding Subunits: Synthesis, Antitumor Activity, and Preliminary Toxicity Study", J. Med. Chem. 46:634-637 (2003).
Zhao R Y et al., "Synthesis and Biological Evaluation of Antibody Conjugates of Phosphate Prodrugs of Cytotoxic DNA Alkylators for the Targeted Treatment of Cancer", Journal of Medicinal Chemistry 55:766-782 (2012).
International Search Report dated Mar. 6, 2015 received in International Application No. PCT/EP2014/069681.

* cited by examiner

THIENO[2,3-E]INDOLE DERIVATIVES AS NEW ANTITUMOR AGENTS

The present invention relates to a novel class of alkylating agents comprising a thieno[2,3-e]indole moiety tethered to a DNA-binding moiety, methods for their preparation, pharmaceutical composition containing them and use thereof in treating certain mammalian tumors.

A wide range of chemicals is now available to treat cancers. Despite the efforts in anticancer research, cancer remains a looming and elusive target; therefore there is still a need for new anticancer agents.

Alkylating agents are cytotoxic agents that have been used for the treatment of cancer for over six decades, yet their repertoire continues to grow. These agents act during all phases of the cell cycle directly on DNA, causing DNA strand breaks, leading to abnormal base pairing, inhibition of cell division and eventually resulting in cell death.

The present invention provides a novel class of alkylating agents comprising a thieno[2,3-e]indole moiety tethered to a DNA-binding moiety.

Thieno[2,3-e]indole derivatives are described in GB2344818 and in Tichenor, M. S. et al., Journal of the American Chemical Society 2007, 129, 14092-99; some specific compounds of the aforementioned documents are excluded from the present general formulas.

Accordingly, a first object of the present invention is to provide a compound of formula (I) or (II)

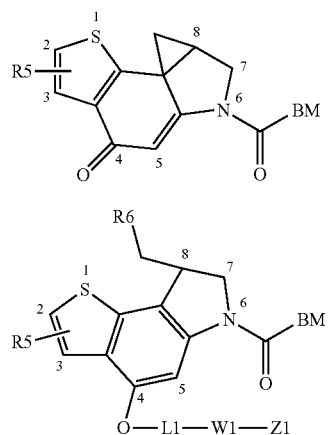

wherein:

R5 is hydrogen, linear or branched $C_1$-$C_4$ alkyl, linear or branched $C_1$-$C_4$ hydroxyalkyl or linear or branched $C_1$-$C_4$ aminoalkyl;

R6 is halogen;

BM is a DNA binding moiety of formula (V):

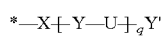 (V)

wherein:

X is null or linear or branched $C_2$-$C_4$ alkenyl;

Y and Y' are independently an optionally substituted aryl or heteroaryl;

U is a moiety of formula (VI) or (VII):

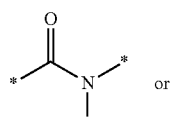

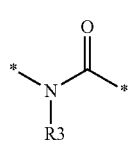

wherein R3 is hydrogen or a group selected from optionally substituted linear or branched $C_1$-$C_4$ alkyl and $C_1$-$C_4$ hydroxyalkyl; and q is an integer from 0 to 3;

L1 is hydrogen or L, wherein L is null or a conditionally-cleavable moiety;

W1 is null or a self-immolative system comprising one or more self-immolative groups; and Z1 is null or a peptidic, non peptidic or hybrid peptidic and non peptidic linker;

provided that a compound of formula (I) or a compound of formula (II) wherein L1 is hydrogen, R5 is methyl and X is null, is excluded when:

1) q is 0 and Y' is a heterocyclyl moiety of formula (VIII), (VIII)' or (VIII)":

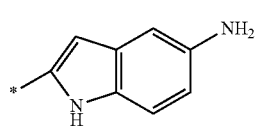

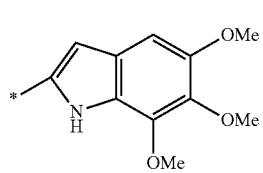

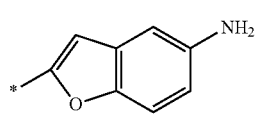

or 2) q is 1, U is a group of formula (VII) as defined above, Y is an heterocyclyl moiety of formula (IX)

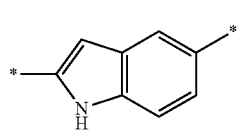

and Y' is an heterocyclyl moiety of formula (VIII)'''

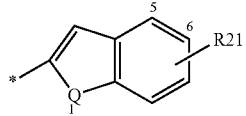

(VIII)''' wherein Q is NH or O, and R21 is hydrogen or a group selected from —N(C$_2$H$_5$)$_2$ and —C(NH)NH$_2$ at the position 5 or 6 of the benzene ring;

and the pharmaceutically acceptable salts thereof.

Cytotoxic drugs act on rapidly proliferating cells with different mechanisms, usually by interfering directly or indirectly with DNA replication. Although this therapy resulted effective in different tumor types, it may suffer from some limitations: interfering with cell proliferation affects indeed also normal cells that proliferate frequently, such as bone marrow, cells of the gastrointestinal tract and hair follicles. Drug concentrations that would completely eradicate the tumor may not be reached because of dose-limiting side effects on these tissues leading immunosuppression, gastrointestinal tract toxicity and hair loss.

In addition cytotoxic drugs show in some cases non optimal physicochemical properties and may lack of suitable pharmacokinetic properties limiting their use in patients.

Conjugation of cytotoxic drugs to molecules able to vehicle the drug and thus improving tumor targeting or able to modify its pharmacokinetic properties is one of the strategies that has been undertaken to solve the above mentioned issues. Different examples of conjugation of cytotoxic drugs with proteins, peptides or aptamer, polymers or nanoparticles allowing better target delivery, improving solubility and in some cases other pharmacokinetic properties such as increasing half life or local concentration of the drug and improving drug performances have been reported.

As a matter of facts, the resultant conjugates have improved characteristics in term of solubility, permeability into the cell, in vivo therapeutic window, controlled release, ability to reach the target according to the nature of the specific molecule conjugated with the cytotoxic agent.

For this reason, there is an increasing demand for the development of functionalized cytotoxic agents suitable to be conjugated with different types of molecules.

The present invention also provides functionalized alkylating agents which, other than having cytotoxic activity, are also suitable to be conjugated with different types of nucleophiles.

In a further aspect, this invention relates to functionalized thieno[2,3-e]indole of formula (III) and (IV)

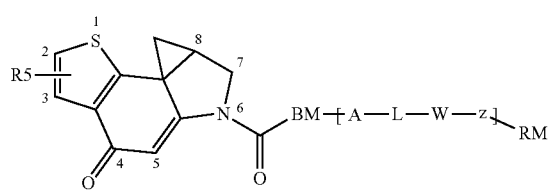

(III)

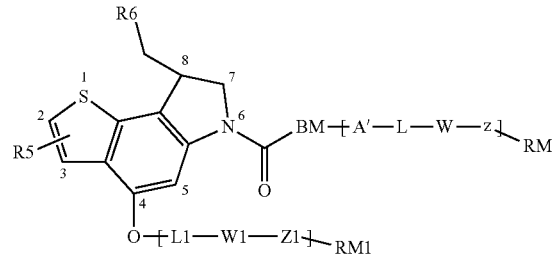

(IV)

wherein:
BM is a DNA binding moiety of formula (V)':

$$*—X\!-\!\!\left[Y\!-\!U\right]_q\!Y'—*$$ (V)' wherein:
X, Y, U, Y' and q are as defined above;
A is an atom selected from —O—, —NH— and —CO—;
A' is null or A, wherein A is as defined above;
L is null or a conditionally-cleavable moiety;
W is null or a self-immolative system comprising one or more self-immolative groups;
Z is null or a peptidic, non peptidic or hybrid peptidic and non peptidic linker;
RM is null or a reactive moiety attached to at least one of the groups selected from A, L, W or Z;
RM1 is null or a reactive moiety attached to at least one of the groups selected from L1, W1 or Z1; and
R5, R6, L1, W1 and Z1 are as defined above;
provided that:
1) in a compound of formula (III) at least one of L, W, Z or RM is not null;
2) in a compound of formula (IV):
  a) when L1 is hydrogen, then A' is not null and at least one of L, W, Z or RM is not null;
  b) when A' is null, then L, W and Z are null, and RM1 is not null;
and the pharmaceutically acceptable salts thereof.

It is noted that when L1 is hydrogen or a conditionally-cleavable moiety, and the O-L1 bond or the O—W1 bond or the O—Z1 bond or O-RM1 bond is broken, so generating a OH function, then the compounds of formula (II) or (IV) may be transformed in a compound of formula (I) or (III) respectively, through the well reviewed reaction mechanism reported in the literature (see e.g. Baiard, R; et al., J. Am. Chem. Soc. 1963, 85, 567-578; Zhao, R. Y. et al. J. Med. Chem. 2012, 55, 766-782.)

In addition, it is to be noted that a compound of formula (III) has one functionalization site

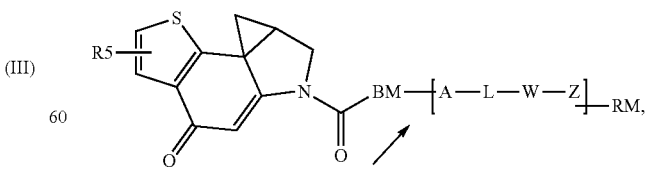

(III)

while a compound of formula (IV) may have one or two functionalization site(s).
Specifically, a compound of formula (IV) has one functionalization site when:

A' is A and L1 is hydrogen, as in a compound of formula (IV)'

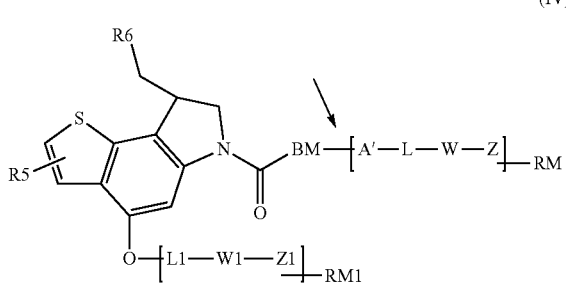

(IV)' or

A' is null and L1 is not hydrogen, as in a compound of formula (IV)'''

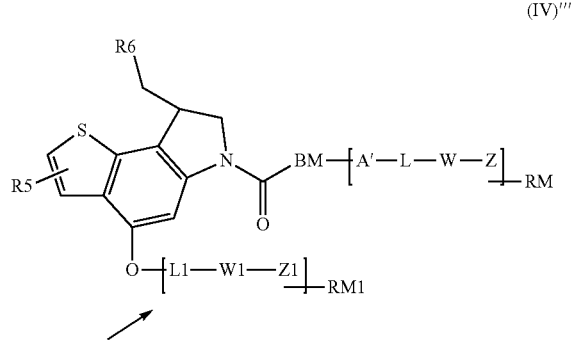

(IV)''' since L, W, Z and/or RM cannot be attached directly to BM.

A compound of formula (IV) has two functionalization sites when:

A' is A and L1 is L, as in a compound of formula (IV)''

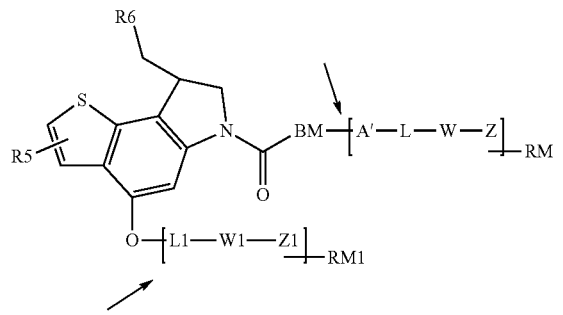

(IV)''

The present invention also provides methods of synthesizing the compounds of formula (I), (II), (III) and (IV), prepared through a process consisting of standard synthetic transformations, and isomers, tautomers, hydrates, solvates, complexes, metabolites, prodrugs, carriers, N-oxides.

The present invention also provides a method for treating cancer, which comprises administering to a mammal, in need thereof, an effective amount of a compound of formula (I), (II), (III) or (IV) as defined above. The mammal in need thereof may be for example a human.

The present invention also provides a compound of formula (I), (II), (III) or (IV), as defined above, for use in a method of treating cancer, cellular proliferation disorders and viral infections.

Preferably, a compound of formula (I), (II), (III) or (IV), as defined above, is for use in a method of treating specific types of cancers, including but not limited to: carcinoma such as bladder, breast, colon, kidney, liver, lung, including small cell lung cancer, esophagus, gall-bladder, ovary, pancreas, stomach, cervix, thyroid, prostate, and skin carcinoma, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukaemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma.

Furthermore, a compound of formula (I), (II), (III) or (IV), as defined above is for use in a method of treating specific cellular proliferation disorders such as, for example, benign prostate hyperplasia, familial adenomatosis polyposis (FAP), neurofibromatosis, psoriasis, vascular smooth cell proliferation associated with atherosclerosis, pulmonary fibrosis, arthritis, glomerulonephritis and post-surgical stenosis and restenosis.

In addition, a compound of formula (I), (II), (III) or (IV), as defined above, is for use in a method of inhibiting tumor angiogenesis and metastasis, as well as in a method of treating organ transplant rejection and host versus graft disease.

The present invention also provides a pharmaceutical composition comprising a therapeutically effective amount of compounds of formula (I), (II), (III) or (IV) or a pharmaceutically acceptable salt thereof as defined above and at least one pharmaceutically acceptable excipient, carrier and/or diluent.

The present invention further provides a pharmaceutical composition comprising a compound of formula (I), (II), (III) or (IV) and one or more chemotherapeutic agents.

The present invention further provides a pharmaceutical composition comprising a compound of formula (I), (II), (III) or (IV) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix-metalloprotease inhibitors, telomerase inhibitors, tyrosine kinase inhibitors, anti-growth factor receptor agents, anti-HER2 agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I), (II), (III), or (IV) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I), (II), (III) or (IV) or a pharmaceutically acceptable salt thereof, as defined above, for use as a medicament.

Moreover the invention provides the use of a compound of formula (I), (II), (III) or (IV) or a pharmaceutically acceptable salt thereof, as defined above, in the manufacture of a medicament with anticancer activity.

Finally, the invention provides the use of a compound of formula (I), (II), (III) or (IV) or a pharmaceutically acceptable salt thereof, as defined above, in the preparation of conjugates.

BRIEF DESCRIPTION OF THE DRAWINGS

The present disclosure will be better understood by reference to the following drawings, which are provided as illustrative of certain embodiments of the subject application, and not meant to limit the scope of the present disclosure.

Figure 1:
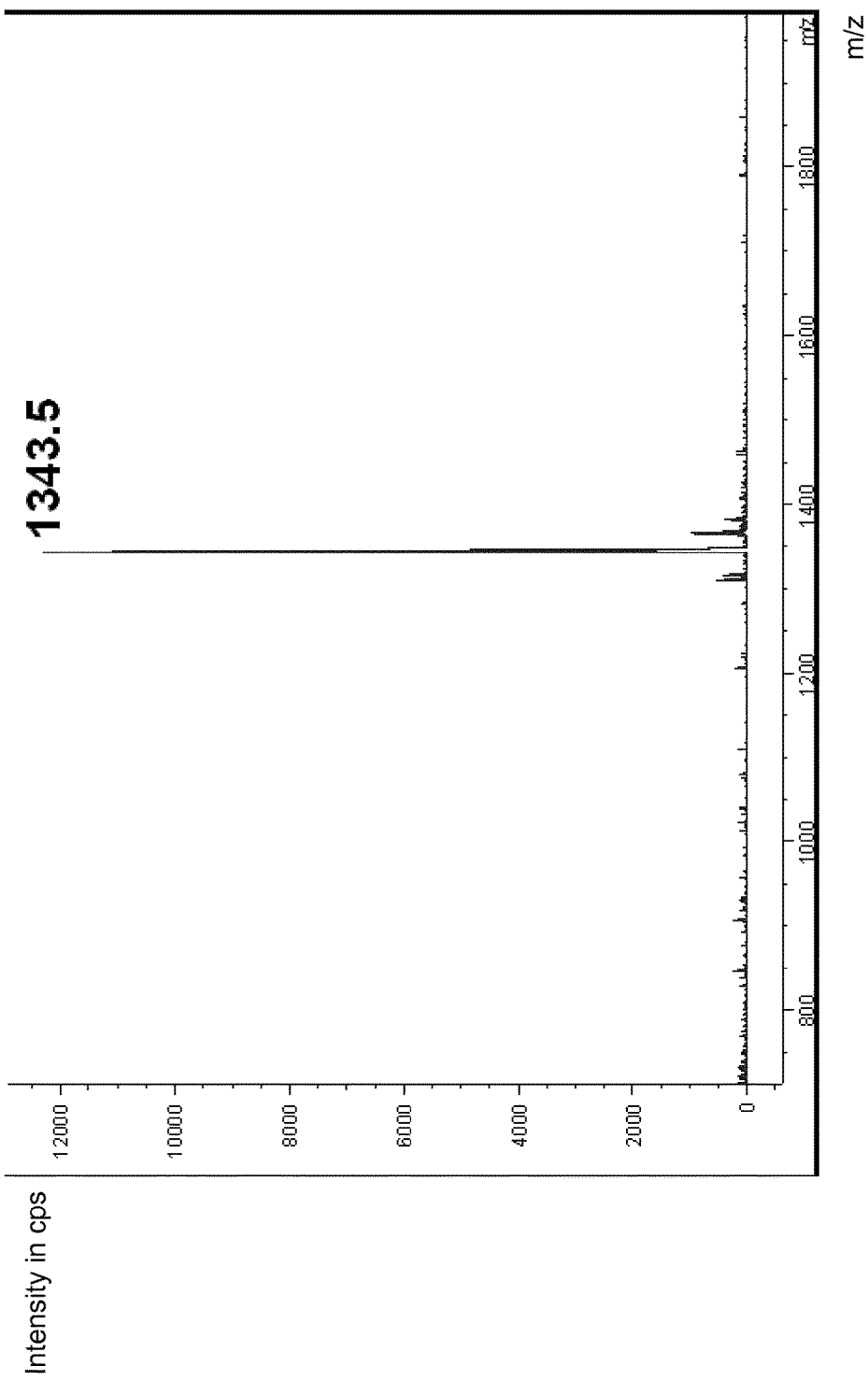
FIG. 1 is a display of a mass spectrum analysis of the conjugate A1, with the molecular weight (m/z) on the x axis, while intensity expressed as counts per second (cps) is reported on the y axis.

Unless stated otherwise, the following terms and phrases as used herein are intended to have the following meanings.

With the term "linear or branched $C_1$-$C_6$ alkyl" we intend any of the groups such as, for instance, methyl, ethyl, n-propyl, isopropyl, n-butyl, isobutyl, sec-butyl, tert-butyl, pentyl, neopentyl, hexyl, etc.

With the term "linear or branched $C_1$-$C_6$ alkoxy", we intend any of the groups such as, for instance, methoxy, ethoxy, propoxy, etc.

With the term "linear or branched $C_1$-$C_4$ alkyl" we intend any of the groups such as, for instance, methyl, ethyl, n-propyl, isopropyl, n-butyl, isobutyl, sec-butyl, tert-butyl.

With the term "linear or branched $C_1$-$C_4$ hydroxyalkyl" we intend a hydrocarbon group having 1 to 4 carbon atoms bearing an hydroxyl group such as, for instance, hydroxymethyl, 2-hydroxyethyl, 3-hydroxypropyl, 3-hydroxybutyl, 2-hydroxybutyl and the like.

With the term "linear or branched $C_1$-$C_4$ haloalkyl" we intend a hydrocarbon group having 1 to 4 carbon atoms bearing an halogen atom such as chlorine, bromine or fluorine. Non limiting examples of such groups are chloromethyl, 2-chloroethyl, 3-chloropropyl, 3-chlorobutyl, fluoromethyl, 2-fluoroethyl, 3-fluoropropyl, 3-fluorobutyl, bromomethyl, 2-bromoethyl, 3-bromopropyl, 3-bromobutyl and the like.

With the term "linear or branched $C_1$-$C_4$ aminoalkyl" we intend any of the groups such as, for instance, 2-aminoethyl, 3-aminopropyl, 4-aminobutyl, 3-aminobutyl, etc.

With the term "linear or branched $C_1$-$C_4$ sulphydylalkyl" we intend a hydrocarbon group having 1 to 4 carbon atoms bearing a sulfhydyl group such as, for instance, mercaptomethyl, 2-mercaptoethyl, 3-mercaptopropyl, 3-mercaptobutyl, 2-mercaptoybutyl and the like.

The term "$C_3$-$C_8$ cycloalkyl" as used herein refers to a saturated or unsaturated non-aromatic all-carbon monocyclic ring, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

With the term "$C_2$-$C_4$ alkenyl" we intend a branched or unbranched unsaturated hydrocarbon group having 2 to 4 carbon atoms and a double bond in any position, such as, for instance, ethenyl, 1-propenyl, 2-propenyl, 1-methyl-ethenyl, 1-butenyl, 2-butenyl, 3-butenyl, etc.

With the term "halogen" we intend a fluorine, chlorine, bromine or iodine.

The term "aryl" as used herein refers to a mono-, bi- or poly-carbocyclic hydrocarbon from 1 to 2 ring systems, optionally further fused or linked to each other by single bonds, wherein at least one of the carbocyclic rings is aromatic, wherein the term "aromatic" refers to completely conjugated π-electron bond system. Non limiting examples of such aryl groups are phenyl, α- or β-naphthyl groups.

The term "heteroaryl" as used herein refers to aromatic heterocyclic rings, typically 4- to 7-membered heterocycles, with from 1 to 4 heteroatoms selected among oxygen, nitrogen and sulfur, wherein nitrogen and sulfur may optionally be oxidized and nitrogen may optionally be quaternized; said heteroaryl ring can be optionally further fused or linked to one or two or more rings fused together, aromatic and non-aromatic carbocyclic and heterocyclic rings. Heteroatoms may be directly connected to each other. Examples of heteroaryl groups include, but are not limited to, pyridinyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises from 1 to 4 heteroatoms. It should be noted that "$C_1$ heteroaryl group" denotes that there is only one carbon present in the ring system of the heteroaromatic group (carbon atoms in optional substituents are thus not counted). An example of such a heteroaromatic group is a tetrazolyl group.

The term "heterocyclyl" as used herein refers to a saturated or unsaturated non-aromatic $C_4$-$C_8$ carbocyclic ring which may consist of one ring or two or more rings fused together, wherein from 1 to 4 carbon atoms are replaced by heteroatoms such as nitrogen, oxygen, sulfur, wherein said heteroatoms may be directly connected to each other; nitrogen and sulfur may optionally be oxidized and nitrogen may optionally be quaternized. Non limiting examples of heterocyclyl groups are, for instance, tetrahydrofuranyl, pyrrolidinyl, piperidinyl, 1,4-dioxanyl, decahydroquinolinyl, piperazinyl, oxazolidinyl and morpholinyl.

The term "leaving group" refers to a group that can be substituted by another group in a substitution reaction. Such leaving groups are well-known in the art and examples include, but are not limited to, an halide (fluoride, chloride, bromide, and iodide), an azide, a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, a carboxylate, an aminocarboxylate (carbamate) and an alkoxycarboxylate (carbonate). For substitutions at saturated carbon, halides and sulfonates are preferred leaving groups. For substitutions at a carbonyl carbon, a halide, succinimide-N-oxide, p-nitrophenoxide, pentafluorophenoxide, tetrafluorophenoxide, carboxylate or alkoxycarboxylate (carbonate) may for example be used as a leaving group. The term "leaving group" also refers to a group that is eliminated as a consequence of an elimination reaction, e.g., an electronic cascade reaction or a spirocyclization reaction. In this instance, a halide, a sulfonate, an azide, an aminocarboxylate (carbamate) or an alkoxycarboxylate (carbonate) may for example be used as a leaving group.

The term "active ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroxybenzotriazole and 1-hydroxy-7-azabenzotriazole, and groups with comparable leaving capability. Unsubstituted alkyl-based alkoxy groups such as methoxy, ethoxy, isopropoxy, and t-butoxy do not qualify as good leaving groups and methyl, ethyl, isopropyl, and t-butyl esters are therefore not considered to be active esters.

The term "nucleophiles" refers to molecules that bear a nucleophilic group. The term "nucleophilic group" refers to a species that donates an electron-pair to an electrophilic group to form a chemical bond in a chemical reaction. Examples of such nucleophilic groups include, but are not limited to halogens, amines, nitrites, azides, alcohols, alkoxyde anions, carboxylate anions, thiols, thiolates, etc.

The term "electrophilic group" refers to a species that accepts an electron-pair from a nucleophilic group to form a chemical bond in a chemical reaction. Examples of such electrophilic groups include, but are not limited to, esters, aldehydes, amides, ketons, etc.

The term "alkylating moiety" refers to the structure that remain after breaking of one or more cleavable bonds and that may or may not be covalently bound to the nucleic acid strand.

The term "unnatural amino acid" refers to the D-stereoisomer of the naturally occurring amino acid.

Pharmaceutically acceptable salts of the compounds of formula (I), (II), (III) or (IV) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of formula (I), (II), (III) or (IV) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

The DNA-binding Moiety BM

The BM moiety is a binding moiety that binds or associates the compound of formula (I), (II), (III) or (IV) with the double strand of the DNA. The binding moiety can improve affinity properties of the derivatives to the DNA or improve alkylating reactivity of the alkylating agent or target different sequences of the DNA so to modulate target specificity of the compounds.

Preferably, in a compound of formula (I) or (II) the BM moiety is a group of formula (V) as defined above, wherein X is null or an alkenyl group of formula (XIV):

(XIV)

wherein R3, independently the same or different, is as define above;

U and q are as defined above;

Y, if present, is a group selected from:

(XVa)

(XVb)

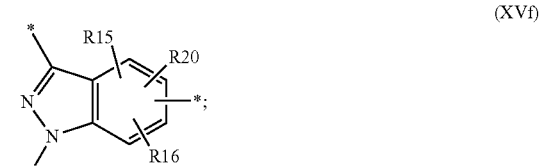

(XVf)

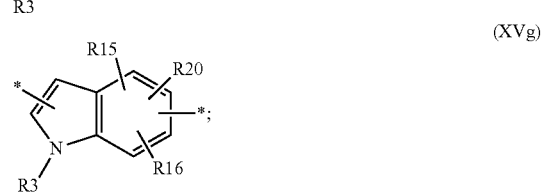

(XVg)

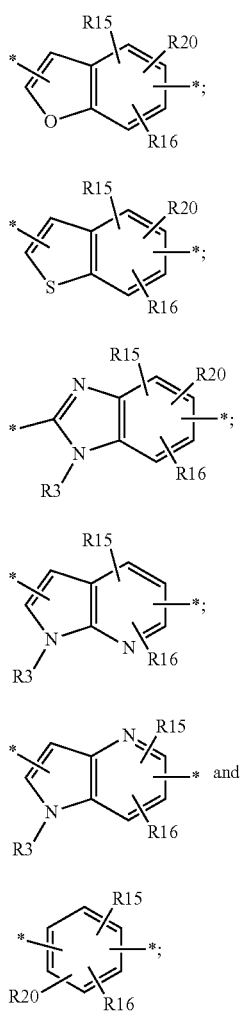

and
Y' is a group selected from:

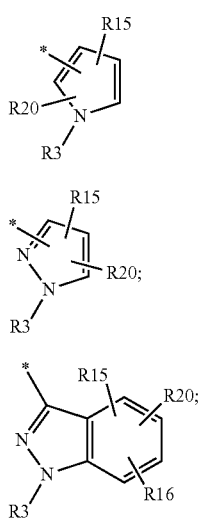

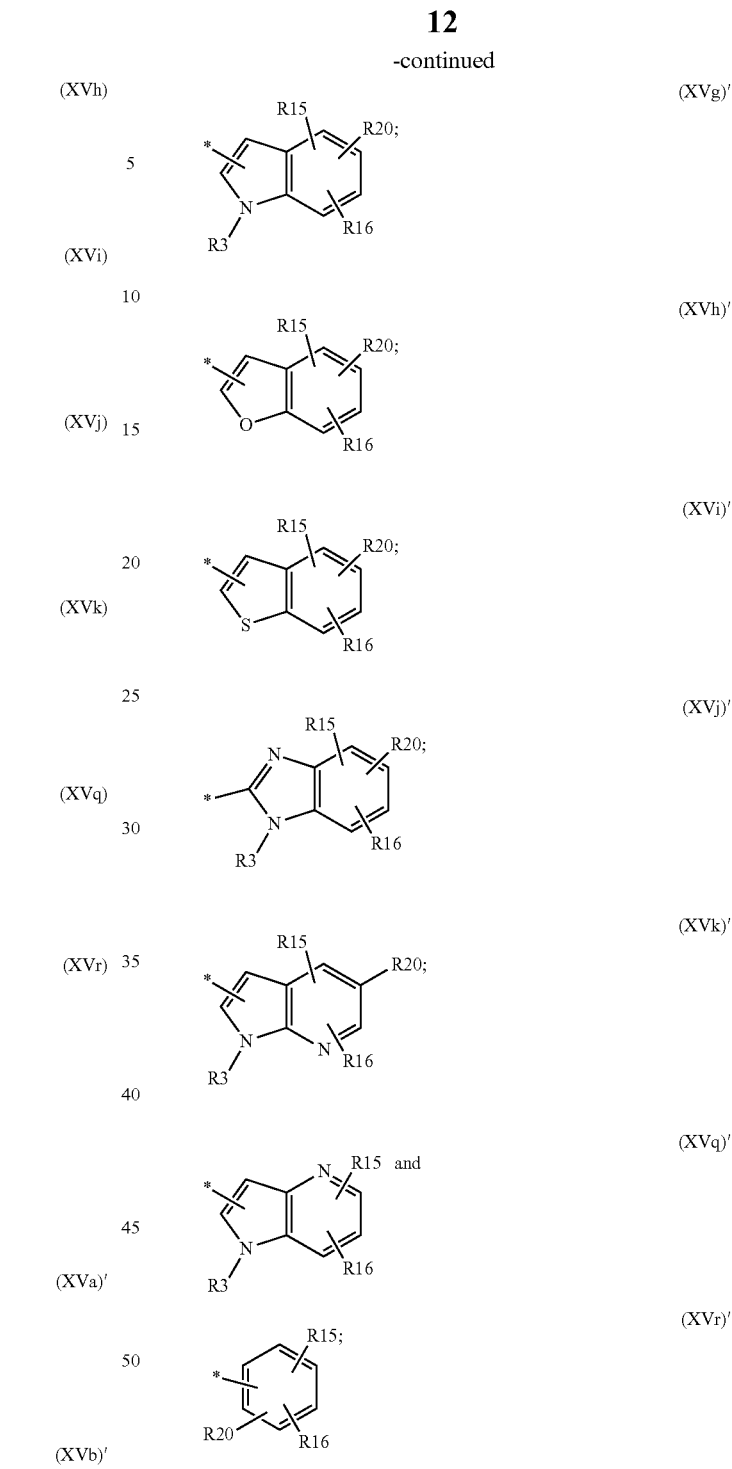

wherein R3 is as defined above, and R15, R16 and R20 are independently hydrogen, hydroxy, —NO$_2$, an optionally substituted linear or branched C$_1$-C$_6$ alkyl or C$_1$-C$_6$ alkoxy, cyano, —COOH, —CONHR22, —NR22R23 or —O—(C$_1$-C$_6$ alkyl)-NR22R23, in which R22 and R23 are independently hydrogen or C$_1$-C$_6$ alkyl or R22 and R23 taken together form a 3 to 7 membered heterocyclyl.

More preferably, in a compound of formula (I) or (II) the BM moiety is a group of formula (V) as defined above, wherein X and U are as defined above;

q is an integer from 0 to 2;

Y, if present, is a group selected from

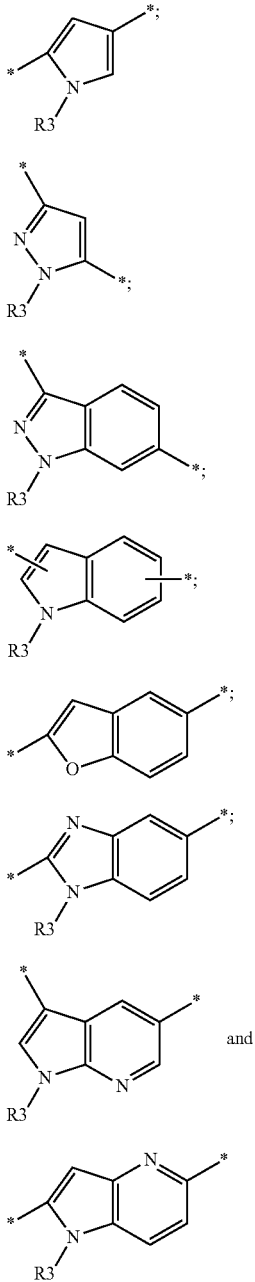

wherein R3 is as defined above;
and
Y' is a group selected from:

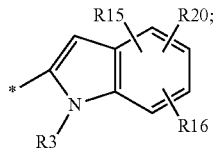
(XVa)''

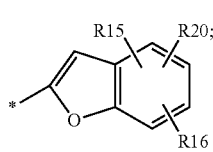
(XVb)''

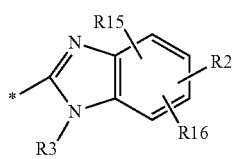
(XVf)''

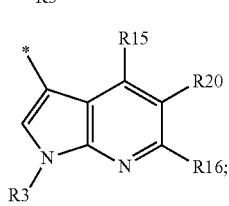
(XVg)''

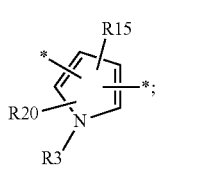
(XVh)''

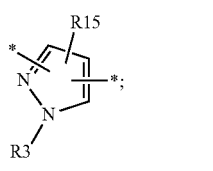
(XVj)''

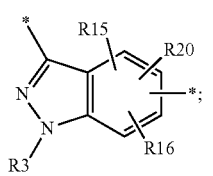
(XVk)''

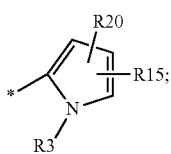
(XVa)'''

(XVg)'''

(XVh)'''

(XVj)''' and (XVk)''' wherein R3 is as defined above, and R15, R16 and R20 are independently hydrogen or an optionally substituted linear or branched $C_1$-$C_6$ alkyl or $C_1$-$C_6$ alkoxy, —CONHR22 or —O—($C_1$-$C_6$ alkyl)-NR22R23 in which R22 and R23 are as defined above.

Preferably, in a compound of formula (III) or (IV), the BM moiety is a group of formula (V)' as defined above, wherein X is null or a $C_2$-$C_4$ alkenyl of formula (XIV) as defined above;

U and q are as defined above;
and

Y, if present, and Y' are independently selected from a group of formula:

(XVa)

(XVb)

(XVf)

-continued (XVg)
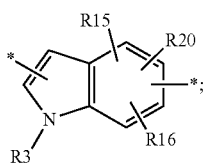

(XVh)
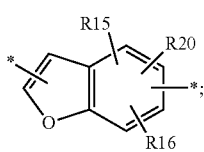

(XVi)
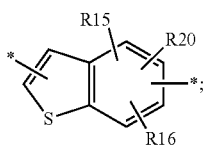

(XVj)
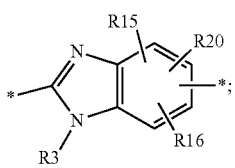

(XVk)
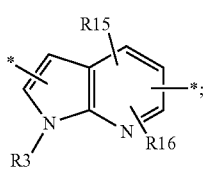

(XVq)
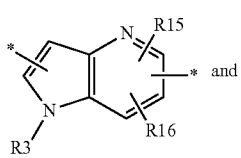

(XVr)
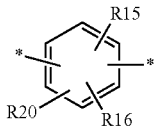

wherein R3 is as defined above, and R15, R16 and R20 are independently hydrogen, hydroxy, —NO₂, an optionally substituted linear or branched $C_1$-$C_6$ alkyl or $C_1$-$C_6$ alkoxy, cyano, —COOH, —CONHR22, —NR22R23 or —O—($C_1$-$C_6$ alkyl)-NR22R23, in which R22 and R23 are independently hydrogen or $C_1$-$C_6$ alkyl or R22 and R23 taken together form a 3 to 7 membered heterocyclyl.

More preferably, in a compound of formula (III) or (IV), the BM moiety is a group of formula (V)' as defined above, wherein X and U are as defined above;

q is an integer from 0 to 2;

Y, if present, is selected from (XVa)″
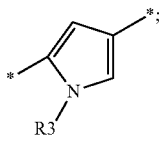

(XVb)″
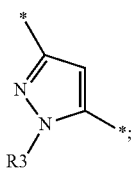

(XVf)″
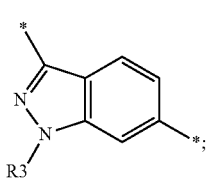

(XVg)″
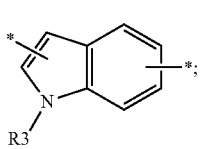

(XVh)″
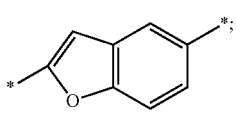

(XVj)″
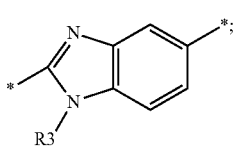

(XVk)″
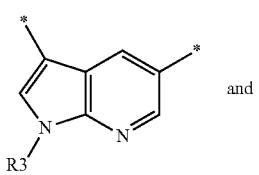

(XVq)″
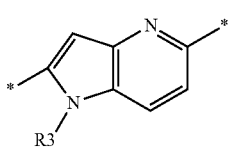

wherein R3 is as defined above; and

Y' is a group selected from:

(XVa)
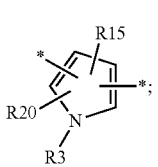

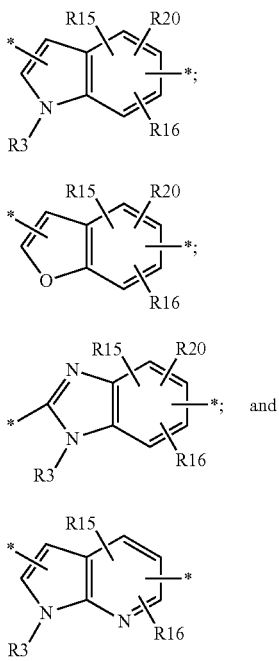

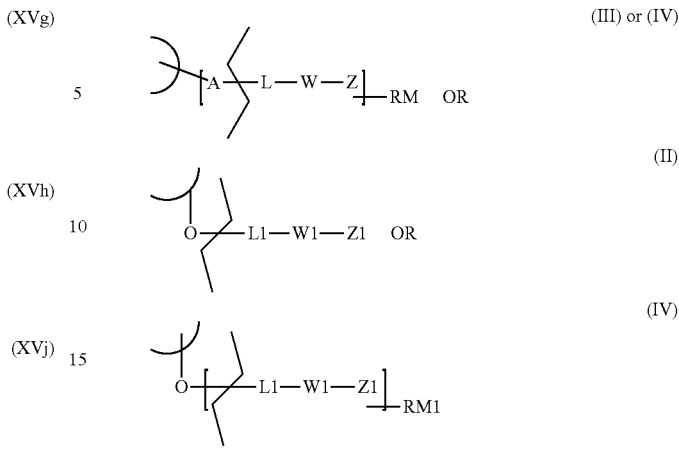

wherein R3 is as defined above, and R15, R16 and R20 are independently hydrogen or an optionally substituted linear or branched $C_1$-$C_6$ alkyl or $C_1$-$C_6$ alkoxy, —CONHR22 or —O—($C_1$-$C_6$ alkyl)-NR22R23 in which R22 and R23 are as defined above.

The Conditionally-cleavable Moiety L or L1

The L or L1 moiety, if present, is a conditionally-cleavable group that can be cleaved by a chemical, photochemical, physical, biological or enzymatic process upon being brought in or under certain conditions. One of these conditions may for example be bringing a compound of the invention in an aqueous environment, which leads to hydrolysis of L and/or L1, or bringing a compound of the invention in an environment that contains an enzyme that recognizes and cleaves L and/or L1, or bringing a compound of the invention under reducing conditions, which leads to reduction and/or removal of L and/or L1, or bringing a compound of the invention under oxidizing conditions, which leads to oxidation and removal of L and/or L1, or bringing a compound of the invention in contact with radiation, e.g., UV light, which leads to cleavage, or bringing a compound of the invention in contact with heat, which leads cleavage of L and/or L1. These conditions may be met directly after administrating a compound of this invention to an animal, e.g., a mammal, for example a human, due to the presence of ubiquitous enzymes in the circulation. Alternatively, said conditions may be met when the compound localizes to a specific organ, tissue, cell, subcellular target, or bacterial, viral, or microbial target, for example by the presence of internal factors (e.g., target-specific enzymes or hypoxia) or application of external factors (e.g., radiation, magnetic fields).

Cleavage of L or L1 means that the bond between A and L in a compound of formula (III) or in a compound of formula (IV) wherein A' is A, or between the oxygen and L1 in a compound of formula (II) or (IV) is broken:

It is noted that in a compound of formula (IV), two conditionally-cleavable groups can be present. In this case the two moieties may or may not be the same and may or may not require the same conditions for cleavage.

In one embodiment, L and/or L1 can be moieties that are cleaved by an enzyme or hydrolytic conditions present in the vicinity or inside the target cells as compared to other parts of the body, or by an enzyme or hydrolytic conditions, present only in the vicinity of or inside the target cells. It is important to recognize that if target site specificity is achieved solely based upon the selective transformation and/or cleavage of said L and/or L1 at the target site, the condition causing the cleavage should preferably, at least to a certain degree, be target site-specific.

In one embodiment, cleavage of L and/or L1 occurs intracellularly.

In another embodiment, cleavage of L and/or L1 occurs extracellularly.

In another embodiment, cleavage of L and/or L1 can occur by a ubiquitous intracellular enzyme.

In one preferred embodiment L and/or L1 may be a moiety that can be cleaved by ubiquitous enzymes, e.g., esterases that are present in the circulation or intracellular enzymes, such as for example proteases and phosphatases, or by pH-controlled hydrolysis. L and/or L1 may therefore form, optionally together with the connecting atom(s) A or oxygen, a carbamate, urea, ester, amide, imine, hydroxylamino, ether, or phosphate group that can be cleaved in vivo.

In a more preferred embodiment A is —O—, and L and L1 are independently null or a group selected from:
—NHCO—R9(Xa); —NHCOO—R9(Xc); —NH—R9 (Xd);

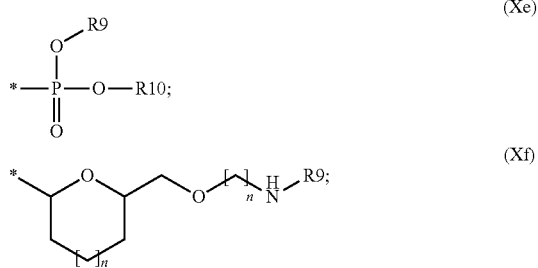

-continued

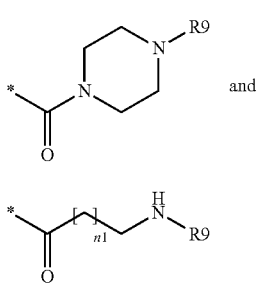

(Xj)

(Xk)

wherein:
R9 and R10 are, each independently, null, hydrogen, hydroxy or a group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;
each of n is independently an integer from 0 to 2 and n1 is an integer from 0 to 4.

In another more preferred embodiment A is —N—, L is null or a group selected from:

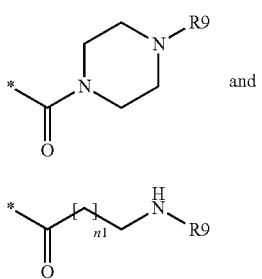

(Xj)

(Xk)

wherein:
R9 and n1 are as defined above, and
L1 is null or a group selected from (Xa), (Xc), (Xd), (Xe), (Xf), (Xj) and (Xk) as defined above.

In another more preferred embodiment A is null and L1 is a group (Xa), (Xc), (Xd), (Xe), (Xf), (Xj) and (Xk) as defined above.

In another more preferred embodiment A is —CO—, L is null or a group selected from:

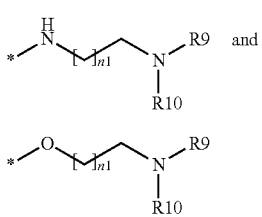

(Xm)

(Xn)

wherein:
R9, R10, and n1 are as defined above and
L1 is null or a group selected from (Xa), (Xc), (Xd), (Xe), (Xf), (Xj) and (Xk), as defined above.

In another more preferred embodiment A' is null and L1 is a group selected from (Xa), (Xc), (Xd), (Xe), (Xf), (Xj) and (Xk) as defined above.

The Self-immolative System W or W1

The W or W1 group, if present, is a self-immolative system that in a compound of formula (III) and (IV) tethers in a stable way from one side a moiety L or A (if L is null), to a moiety Z or RM (if Z is null); in a compound of formula (II) tethers in a stable way from one side a moiety L1 or oxygen (if L1 is null), to Z1 or additionally to RM1 (if Z1 is null) in compound of formula (IV). The L-W, A-W, L1-W1 or O—W1 bond can become labile upon activation by a chemical, photochemical, physical, biological or enzymatic process upon being brought in or under certain condition, as described above, leading optionally to the release of the corresponding moieties:

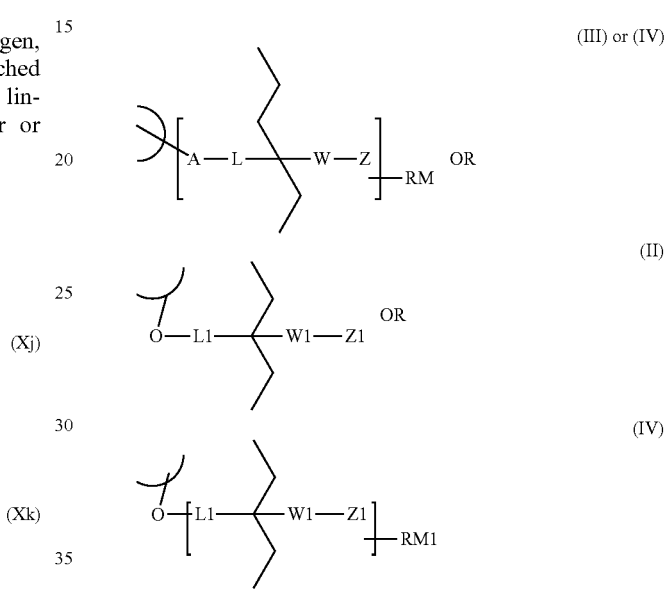

It is noted that in compound of formula (IV), two self-immolative systems can be present. In this case the two systems may or may not be the same and may or may not require the same conditions for cleavage.

A self-immolative system may be incorporated in a compound of formula (II), (III) or (IV) for example to improve solubility or to improve space between the alkylating moiety and the reactive moiety; in addition said self-immolative system can modulate the reactivity of RM or RM1 versus nucleophfiles.

Self-immolative systems are known to the person skilled in the art, see for example those described in WO2002/083180 and WO2004/043493; or those described in Tranoy-Opalinsi, A. et al., Anticancer Agents in Medicinal Chemistry, 2008, 8, 618-637. Other examples of self-immolative systems include, but are not limited to, optionally substituted 4-aminobutyric acid amides, appropriately substituted bicyclo[2.2.1] and bicyclo[2.2.2] ring systems or 2-aminophenylpropionic acid amides (see WO 2005/079398, WO 2005/105154 and WO 2006/012527; Greenwald, R. B., et al., Adv. Drug Delivery Rev. 2003, 55, 217-250; Kingsbury, W. D.; et al., J. Med. Chem. 1984, 27, 1447-1451).

In one preferred embodiment W or W1 may form, together with the connecting atom(s) L, L1, A, Z, Z1, RM, RM1 or oxygen, a carbonate, a carbamate, an urea, an ester, an amide or an ether linkage group that can be optionally cleaved upon activation.

In a preferred embodiment, W and W1 are independently null or a self-immolative system, comprising one or more self-immolative groups independently selected from:

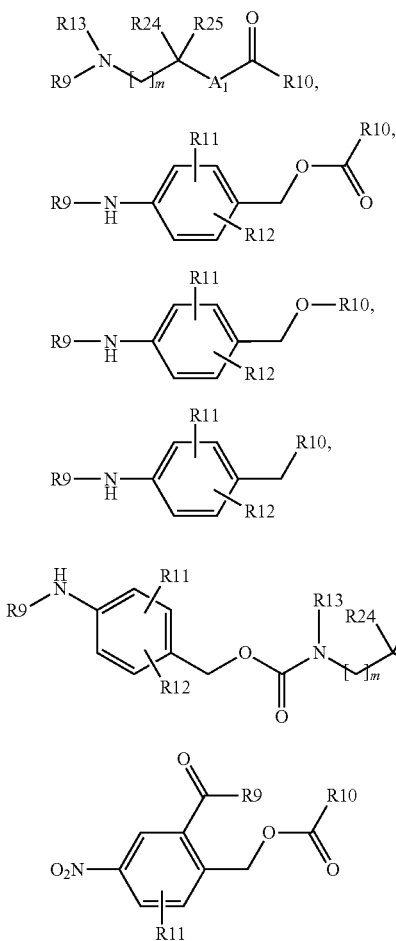

(XIa)

(XIc)

(XId)

(XIk)

(XIj)

(XIf)

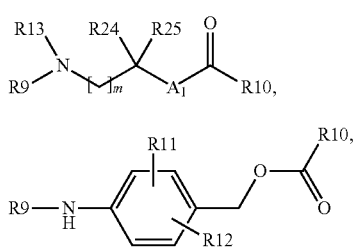

wherein
one of R9 and R10 is null and the other is as defined above;
R11 and R12 are, each independently, hydrogen, halogen, linear or branched $C_1$-$C_4$ alkyl or linear or branched $C_1$-$C_4$ hydroxyalkyl;
R24 and R25 are, each independently, hydrogen, halogen, methyl, ethyl, linear or branched $C_1$-$C_4$ hydroxyalkyl, linear or branched $C_1$-$C_4$ haloalkyl, or R24 and R25 taken together form a 3 to 6 membered carbocycle;
m is an integer from 0 to 3; and
$A_1$ is $CH_2$, $CH_2N$—R13 or N—R13, wherein R13 is hydrogen, linear or branched $C_1$-$C_4$ alkyl, linear or branched $C_1$-$C_4$ hydroxyalkyl or linear or branched $C_1$-$C_4$ haloalkyl;
In a more preferred embodiment, W and W1 are independently null or a group selected from:

(XIa)

(XIc)

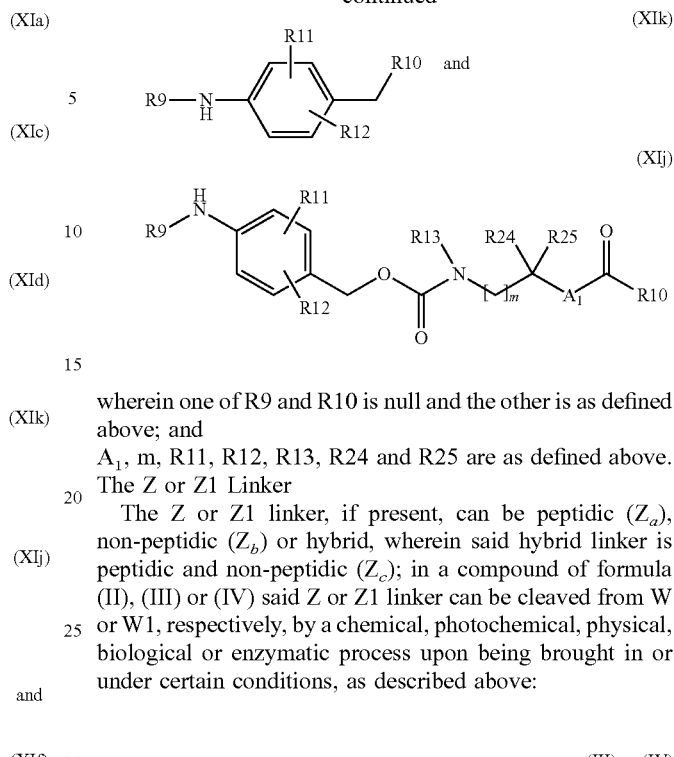

(XIk)

(XIj)

wherein one of R9 and R10 is null and the other is as defined above; and
$A_1$, m, R11, R12, R13, R24 and R25 are as defined above.

The Z or Z1 Linker

The Z or Z1 linker, if present, can be peptidic ($Z_a$), non-peptidic ($Z_b$) or hybrid, wherein said hybrid linker is peptidic and non-peptidic ($Z_c$); in a compound of formula (II), (III) or (IV) said Z or Z1 linker can be cleaved from W or W1, respectively, by a chemical, photochemical, physical, biological or enzymatic process upon being brought in or under certain conditions, as described above:

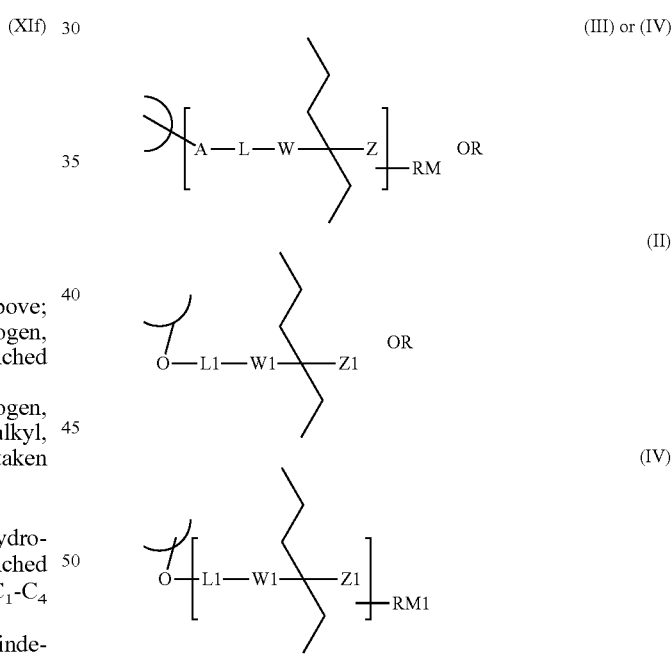

(III) or (IV)

(II)

(IV)

The Z or Z1 linker may be linear or branched.
The linkage between Z or Z1 and its left hand side moiety or between Z or Z1 and, optionally, RM or RM1, may be an ester, an amide, a carbonate, a carbamate, a disulfide or a carbamate linkage.
In one embodiment both of Z and Z1 are null.
In another embodiment one of Z or Z1 is null.
In another embodiment Z and/or Z1 is a peptidic linker $Z_a$ that can be cleaved by a proteolytic enzyme, plasmin, cathepsin, β-glucuronidase, galactosidase, prostate-specific antigen (PSA), urokinase-type plasminogen activator (u-PA) or a member of the family of matrix metalloproteinases.

In another embodiment Z and/or Z1 is a non-peptidic linker $Z_b$ that may contain one or more non-peptidic water-soluble moieties. In this case the linker contributes to the water solubility of a compound of formula (II), (III) or (IV).

In another embodiment $Z_b$ is a non-peptidic linker that may contain one or more non-peptidic moieties that reduce(s) aggregation of a compound of formula (II), (III) or (IV), which may or may not be a moiety/moieties that also increase(s) the water solubility of a compound of formula (II), (III) or (IV).

For example, non-peptidic water-soluble $Z_b$ linkers may contain an oligoethylene glycol or polyethylene glycol moiety or a derivative thereof.

In another embodiment Z and/or Z1 is a hybrid linker $Z_c$ that can contains both, peptidic and non peptidic residues of general formula:

$Z_a$—$Z_b$ wherein $Z_a$ is a peptidic linker and $Z_b$ is a non peptidic linker. Hybrid linkers may contribute to solubility of compound of formula (II), (III) or (IV) and/or be a substrate that can be cleaved by proteolytic enzyme, for example by a member of the family of matrix metalloproteinases.

In a preferred embodiment $Z_a$ is selected from a single amino acid, a dipeptide, a tripeptide, a tetrapeptide, and an oligopeptide moiety comprising natural L-amino acids, unnatural D-amino acids, synthetic amino acids, or any combination thereof, wherein one of the C-terminal or the N-terminal amino acid residue is linked to W, L or A or to W1, L1 or oxygen and, the other terminal amino acid ends with a —COOH or —NH₂ group or is optionally linked to RM or RM1.

In a more preferred embodiment $Z_a$ is a dipeptide or a tripeptide, linked via its C-terminus to W or W1, or to L when W is null, or to L1 when W1 is null, or to A when W and L are both null, or to oxygen when W1 and L1 are both null.

In another more preferred embodiment the C-terminal amino acid residue of the dipeptide or of the tripeptide is selected from glycine, lysine, alanine, arginine and citrulline; and the N-terminal amino acid residue is selected from any natural or unnatural amino acid; preferably, in case of the tripeptide, the middle amino acid residue is selected from leucine, isoleucine, methionine and phenylalanine.

In another more preferred embodiment $Z_a$ comprises a pentapeptide, wherein the C-terminal amino acid is selected from any natural or unnatural amino acid and the N-terminal amino acid residue is 6-aminohexanoic acid.

In a preferred embodiment $Z_b$ may contain an oligoethylene glycol or polyethylene glycol moiety or a derivative thereof.

In a more preferred embodiment $Z_b$ is a group selected from:

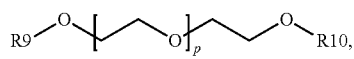
(XIIa)

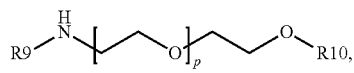
(XIIb)

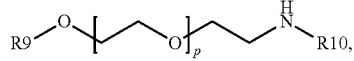
(XIId)

-continued

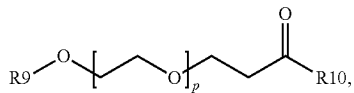
(XIIj)

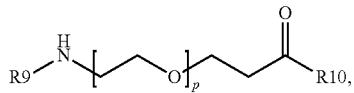
(XIIk)

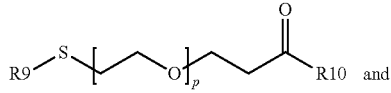
(XIIo)

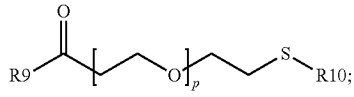
(XIIp)

wherein
one of R9 and R10 is null and the other is as defined above; and
p is an integer from 1 to 20;

In a preferred embodiment $Z_c$ is a hybrid moiety comprising:
a peptidic moiety $Z_a$, wherein $Z_a$ is a single amino acid, a tripeptide or a tetrapeptide, comprising natural L-amino acids and
a non-peptidic moiety $Z_b$ comprising an oligoethylene glycol or polyethylene glycol moiety or a derivative thereof.

The Reactive Moiety RM or RM1

The RM or RM1 moiety, if present, is a reactive group that can react with nucleophiles, i.e. molecules that bear a nucleophilic group, or electrophiles, i.e. molecules that bear a electrophilic group, under relatively mild conditions and without the need of prior functionalization of the reactive moiety; said reaction between the reactive moiety and said nucleophile or electrophile will only require the application of some heat, pressure, a catalyst, acid, and/or base.

Therefore, when one of RM or RM1 moiety is present, a compound of formula (III) o (IV) conjugates with different types of nucleophiles or electrophiles.

When both RM and RM1 moieties are null, a compound of formula (III) or (IV) can conjugate with different types of nucleophiles or electrophiles, through one or more of the nucleophilic groups (e.g. amino, thiol, hydroxyl) or of the electrophilic group (e.g. carboxylic) which are present on the A, L, L1, W, W1, Z and Z1 moiety(ies).

In a compound of formula (III) the RM moiety can be connected to one or more of the A, L, W or Z groups; in a compound of formula (IV) RM can be connected either to one or more of the A', L, W or Z groups and/or to one or more of the L1, W1, Z1 groups or to the oxygen atom:

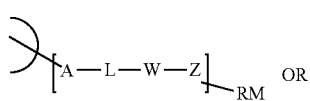
(III) or (IV)

OR

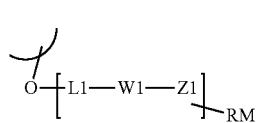
(IV)

Examples of reactive moieties include, but are not limited to, carbamoyl halide, acyl halide, active ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

In one preferred embodiment of the invention, when the nucleophilic group of the nucleophile is NH, NH$_2$, SH or OH, RM and RM1 are independently null or a group selected from:

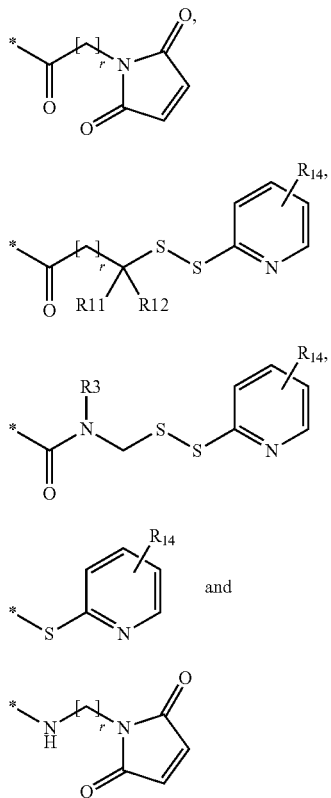

wherein R14 is C$_1$-C$_3$ alkyl or an electron-withdrawing group, preferably NO$_2$ and CN;
r is an integer from 0 to 7; and
R11 and R12 are as defined above, preferably C$_1$-C$_3$ alkyl.

In another preferred embodiment of the invention, when the electrophilic group of the electrophile is COOH, RM and RM1 are independently null or a group selected from:

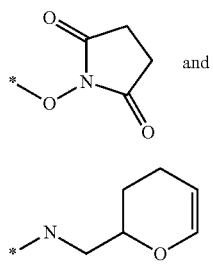

In a most preferred embodiment at least one of RM and RM1 is not null.

Preferably, the present invention provides compounds of formula (I) or (II) as defined above, wherein R5 is linear or branched C$_1$-C$_4$ alkyl.

More preferably, the present invention provides compounds of formula (II) as defined above, characterized in that L1 is hydrogen or a conditionally-cleavable moiety of formula (Xj)

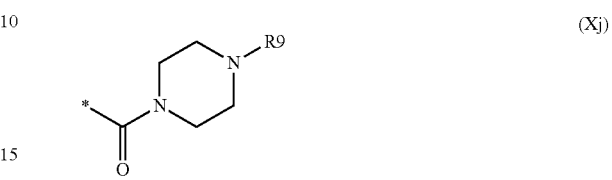

wherein R9 is hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl.

Preferably, the present invention provides compounds of formula (III) or (IV) as defined above, characterized in that R5 is linear or branched C$_1$-C$_4$ alkyl.

More preferably, the present invention provides compounds of formula (IV) as defined above, characterized in that A' is null and L1 is L, wherein L is as defined above.

More preferably, the present invention provides compounds of formula (III) or (IV) as defined above, characterized in that L and L1 are independently null or a conditionally-cleavable moiety selected from:
—NHCO—R9(Xa); —NHCOO—R9(Xc); —NH—R9 (Xd);

$$\underset{(Xe)}{\overset{\overset{R9}{\underset{|}{O}}}{\underset{\underset{O}{\parallel}}{*-P-O-R10;}}}$$

(Xf)

(Xj)

(Xk)

wherein:
R9 and R10 are, each independently, null, hydrogen, hydroxy or an optionally substituted group selected from linear or branched C$_1$-C$_4$ alkyl, linear or branched C$_1$-C$_4$ hydroxyalkyl, linear or branched C$_1$-C$_4$ sulfhydrylalkyl and linear or branched C$_1$-C$_4$ aminoalkyl;
each of n is independently an integer from 0 to 2 and n1 is an integer from 0 to 4.

More preferably, the present invention provides compounds of formula (III) or (IV) as defined above, characterized in that W and W1 are independently a self-immolative system comprising one or more self-immolative groups independently selected from:

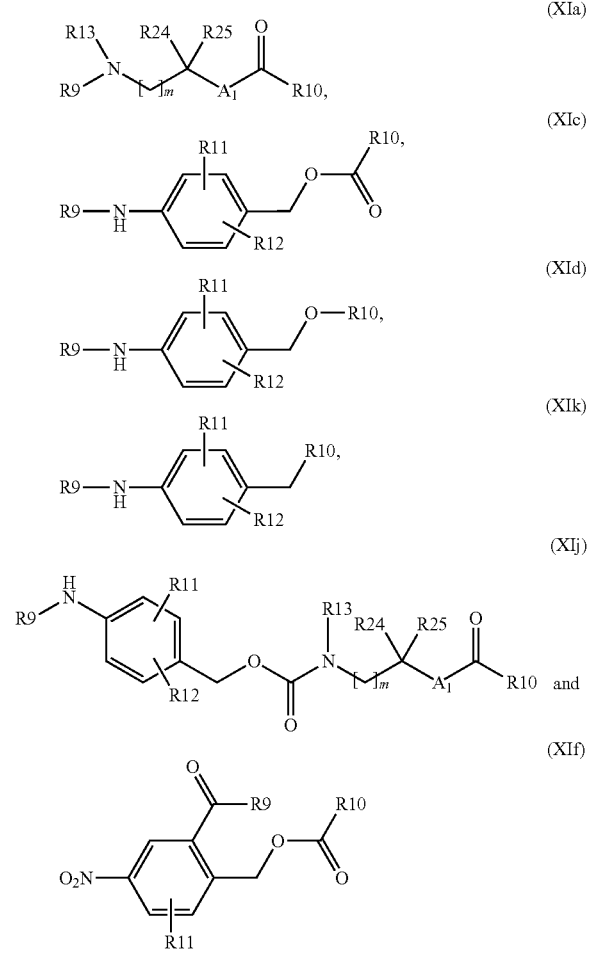

wherein one of R9 and R10 is null and the other is as defined above;

R11 and R12 are, each independently, hydrogen, halogen, linear or branched $C_1$-$C_4$ alkyl or linear or branched $C_1$-$C_4$ hydroxyalkyl;

R24 and R25 are, each independently, hydrogen, halogen, methyl, ethyl, linear or branched $C_1$-$C_4$ hydroxyalkyl, linear or branched $C_1$-$C_4$ haloalkyl, or R24 and R25 taken together form a 3 to 6 membered carbocycle;

m is an integer from 0 to 3; and $A_1$ is $CH_2$, $CH_2$N—R13 or N—R13, wherein R13 is hydrogen, linear or branched $C_1$-$C_4$ alkyl, linear or branched $C_1$-$C_4$ hydroxyalkyl or linear or branched $C_1$-$C_4$ haloalkyl;

More preferably, the present invention provides compounds of formula (III) or (IV) as defined above, characterized in that Z and Z1 are independently a peptidic linker, preferably a dipeptide or a tripeptide linker, or a non peptidic linker containing an oligoethylene glycol or polyethylene glycol moiety or a derivative thereof selected from:

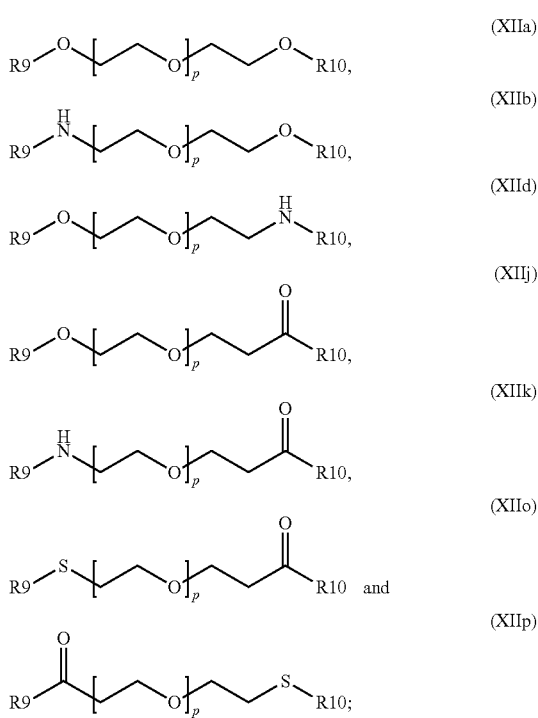

wherein one of R9 and R10 is null and the other is as defined above; and p is an integer from 1 to 20.

More preferably, the present invention provides compounds of formula (III) or (IV) as defined above, characterized in that RM and RM1 are independently a reactive moiety selected from:

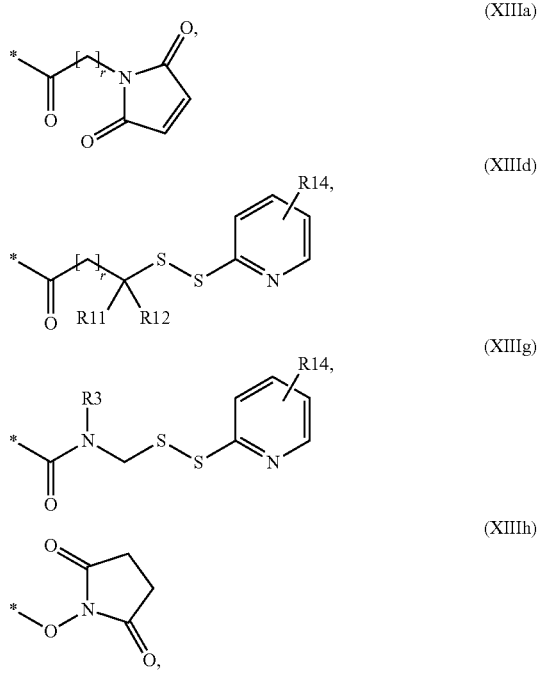

-continued

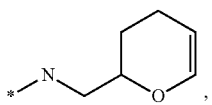
(XIIIi)

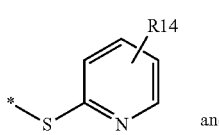
(XIIIj)

and

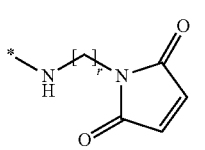
(XIIIm)

wherein R14 is $C_1$-$C_3$ alkyl or an electron-withdrawing group, preferably $NO_2$ and CN;
r is an integer from 0 to 7; and
R11 and R12 are as defined above.

Specific, not limiting, preferred compounds (compd.) of the present invention, optionally in the form of a pharmaceutically acceptable salt, are the following:

[(8S)-8-(chloromethyl)-4-hydroxy-2-methyl-7,8-dihydro-6H-thieno[2,3-e]indol-6-yl]{5-[2-(pyrrolidin-1-yl)ethoxy]-1H-indol-2-yl}methanone (compd 1)

[(8R)-8-(chloromethyl)-4-hydroxy-2-methyl-7,8-dihydro-6H-thieno[2,3-e]indol-6-yl]{5-[2-(pyrrolidin-1-yl)ethoxy]-1H-indol-2-yl}methanone (compd 2)

(7aS,8aS)-2-methyl-6-({5-[2-(pyrrolidin-1-yl)ethoxy]-1H-indol-2-yl}carbonyl)-6,7,7a,8-tetrahydro-4H-cyclopropa[c]thieno[2,3-e]indol-4-one (compd 3)

(7aR,8aR)-2-methyl-6-({5-[2-(pyrrolidin-1-yl)ethoxy]-1H-indol-2-yl}carbonyl)-6,7,7a,8-tetrahydro-4H-cyclopropa[c]thieno[2,3-e]indol-4-one (compd 4)

N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide (compd 5) and N-[6-(2,5-dioxo-2,5-dihydro-1H-pyrrol-1-yl)hexanoyl]-L-valyl-$N^5$-carbamoyl-N-[4-({[{2-[({[(8R)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide (compd 6).

For a reference to any specific compound of the formula (I), (II), (III) or (IV) of the invention, optionally in the form of a pharmaceutically acceptable salt, see the experimental section and claims.

The present invention also provides a process for the preparation of a compound of formula (I), (II), (III) or (IV) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The present invention provides a process for the preparation of a compound of formula (I) or (III) as defined above, characterized in that the process comprises the following step:

a) converting a compound of formula (II) or (IV)

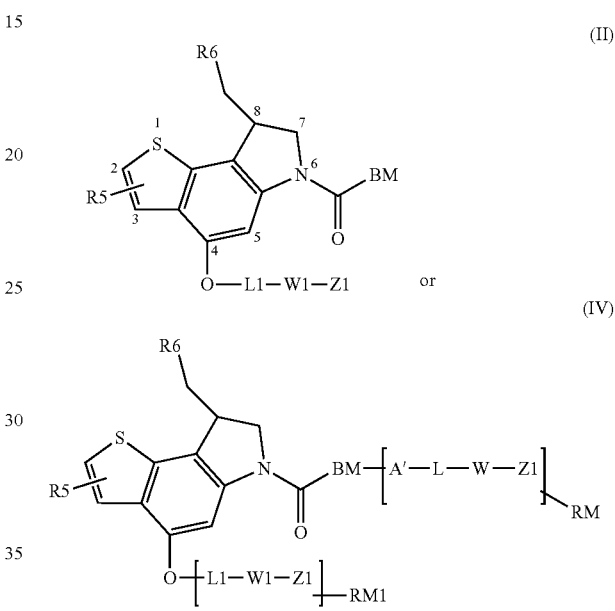

wherein
L1 is hydrogen, W1, Z1 and RM1 are null, and R5, R6, BM, A', L, W, Z and RM are as defined above, to give a compound of formula (I) or (III), respectively as defined above, and the pharmaceutically acceptable salts thereof.

Accordingly, the preparation of a compound of formula (I) or (III) is depicted in Scheme 1 below:

Scheme 1

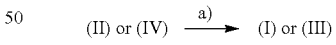

According to step a) the reaction is performed by well known procedures reported in the art (see for example Boger, D. L.; *J. Am. Chem. Soc.* 1996, 118, 2301-2302). An example, that is not intended to limit the method, is the use of basic conditions such as e.g. the use of TEA, $NaHCO_3$ or DBU. The reaction is performed in DCM or DMF or a mixture of them, at a temperature ranging from 20° C. to reflux and for a time ranging from 30 minutes to about 24 hours.

The present invention also provides a process for the preparation of a compound of formula (II) as defined above, i.e. a compound of formula (II)' wherein L1 is hydrogen and a compound of formula (II)'' wherein L1 is not hydrogen, characterized in that the process comprises the following steps:

b) reacting a compound of formula (XVI)

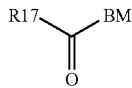

(XVI)

wherein R17 is halogen, OH or an activating moiety of the carboxylic group, e.g. activated esters, and BM is a binding moiety of formula (V) as defined above,
with a compound of formula (XVII)

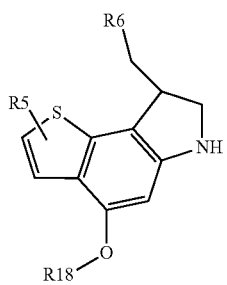

(XVII)

wherein R18 is hydrogen or a protecting group, e.g. benzyl, or an activating group of the OH function, e.g. a triflate (O-Tf) or active ester, and R5 and R6 are as defined above;

optionally, removing the protection if present, then c) reacting the resultant compound of formula (II)'

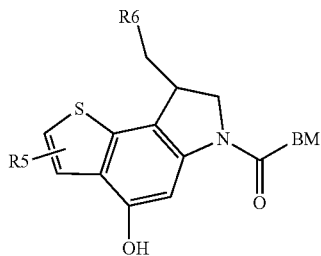

(II)' wherein R5, R6 and BM are as defined above, with a compound of formula (XVIII)

R19-L1-W1-Z1 (XVIII)

wherein R19 is null, hydrogen, O-Tf, an activating moiety of the NH group, preferably tosyl, or R17, wherein R17 is as defined above, and
L1, W1 and Z1 are as defined above and at least one of them is not null, to give a compound of formula (II)"

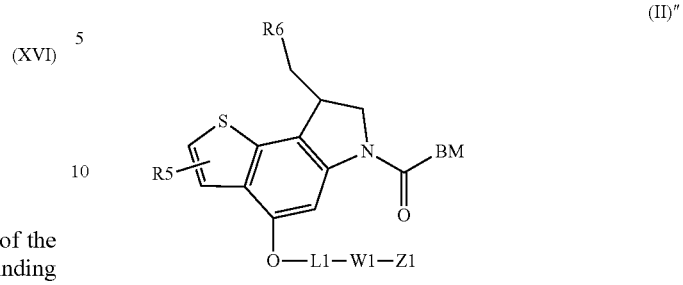

(II)"

wherein L1 is as defined above except hydrogen, at least one of L1, W1 and Z1 is not null, and
R5 and R6 are as defined above,
and the pharmaceutically acceptable salts thereof.

Accordingly, the preparation of a compound of formula (II) is depicted in Scheme 2 below:

Scheme 2

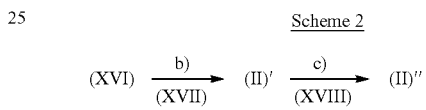

The present invention also provides a process for the preparation of a compound of formula (IV) as defined above, i.e. a compound of formula (IV)' wherein A' is A and L1 is hydrogen and a compound of formula (IV)" wherein A' is A and L1 is not hydrogen, characterized in that the process comprises the following steps:

d) reacting a compound of formula (XIX)

(XIX)

wherein A' is A, wherein A is as defined above and
BM is a binding moiety of formula (V)' as defined above,
with a compound of formula (XX)

(XX)

wherein R19 is as defined above, and
L, W, Z and RM are as defined above and at least one of them is not null;

e) reacting the resultant compound of formula (XXI)

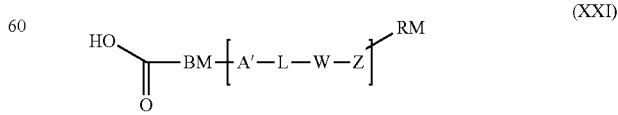

(XXI)

wherein A' is A, wherein A is as defined above, and
BM, L, W, Z and RM are as defined above, with a compound of formula (XVII)

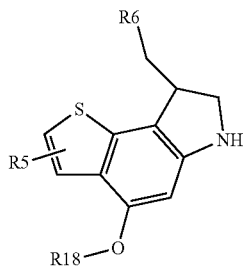

as defined above;
optionally, removing the protection if present, then
f) reacting the resultant compound of formula (IV)'

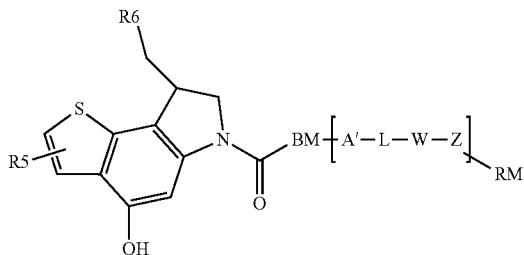

wherein A' is A, wherein A is as defined above,
L, W, Z and RM are as defined above, and at least one of them is not null,
and R5, R6 and BM are as defined above,
with a compound of formula (XX)'

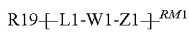

wherein R19 is as defined above, L1 is as defined above except hydrogen, and W1, Z1 and RM1 are as defined above, and at least one of them is not null, to give a compound of formula (IV)"

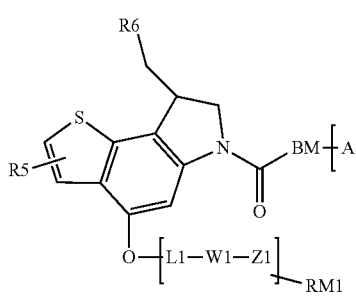

wherein L1 is as defined above except hydrogen,
W1, Z1 and RM1 are as defined above, and at least one of them is not null,
A' is A, wherein A is as defined above,
L, W, Z and RM are as defined above, and
R5, R6 and BM are as defined above,
and the pharmaceutically acceptable salts thereof.

The present invention also provides a process for the preparation of a compound of formula (IV) as defined above, i.e. a compound of formula (IV)' as defined above, and a compound of formula (IVa)" wherein A' is A, wherein A is a saturated group selected from OH, NH$_2$ and COOH, and L1 is not hydrogen, characterized in that the process comprises the following steps:

d') reacting a compound of formula (XIX) with a compound of formula (XVII) as defined above; optionally, removing the protection if present, then e') reacting the resultant compound of formula (XV)

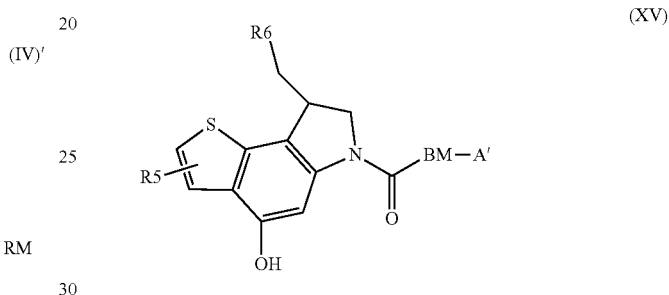

wherein A' is A, wherein A is a saturated group selected from OH, NH$_2$ and COOH
and
R5, R6 and BM are as defined above,
with the compound of formula (XX) as defined above;
optionally
f') reacting the resultant compound of formula (IV)'

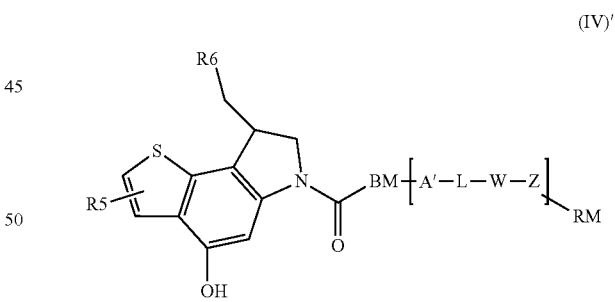

wherein A' is A, wherein A is as defined above, and
R5, R6, BM, L, W, Z and RM are as defined above
with a compound of formula (XX)' defined above so to yield a compound of formula (IV)" as defined above, and the pharmaceutically acceptable salts.
or
e") reacting the compound of formula (XV) as defined above, with the compound of formula (XX)' as defined above; optionally f") reacting the resultant compound of formula (IVa)"

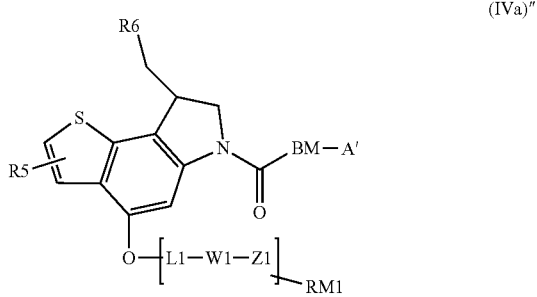

(IVa)"

wherein L1 is as defined above except hydrogen, W1, Z1 and RM1 are as defined above and at least one of them is not null,
A' is A, wherein A is a saturated group selected from OH, $NH_2$ and COOH and R5, R6 and BM are as defined above, with the compound of formula (XX) as defined above, to give a compound of formula (IV)" as defined above, and the pharmaceutically acceptable salts.

Accordingly, the preparation of a compound of formula (IV), i.e. a compound of formula (IV)', (IV)" or (IVa)" as defined above, is depicted in Scheme 3 below:

Scheme 3

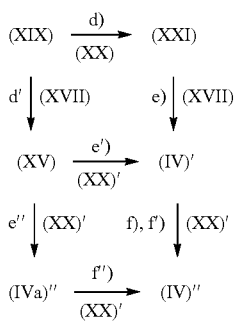

According to steps c), d), f), e'), f'), e") and f") the coupling is performed in a organic solvent, preferably DMF, in presence of a condensing agent such as for example DCC, EDC (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio) or in case of ether bound linking following similar procedure as those reported in *J.O.C.* 2002, 67, 1866-1872; *Bioorg. Med. Chem.* 1996, 4, 1379-1391. See also specific chemical conditions reported in the experimental part below.

According to steps b), e) and d') the coupling reaction is preferably carried out at a temperature ranging from 20° C. to reflux, in presence optionally of a base, and for a time ranging from 30 minutes to about 24 hours.

Compounds of formula (XVII) and (XIX) are known or can be prepared by methods known to the expert in the art or as reported in GB2344818 cited above or J. Med. Chem. 2003, (46) page 634-637.

Compounds of formula (XVI), (XVIII), (XX) and (XX)' are known or can be prepared by methods known to the expert in the art or as reported in Anticancer Agents in Med Chem 2008, (8) page 618-637 or in WO2010/009124.

The present invention also provides a process for the preparation of a compound of formula (IV) as defined above,
i.e. a compound of formula (IV)''' wherein A' is null and L1 is not hydrogen, characterized in that the process comprises the following step:

e''') reacting a compound of formula (II)'

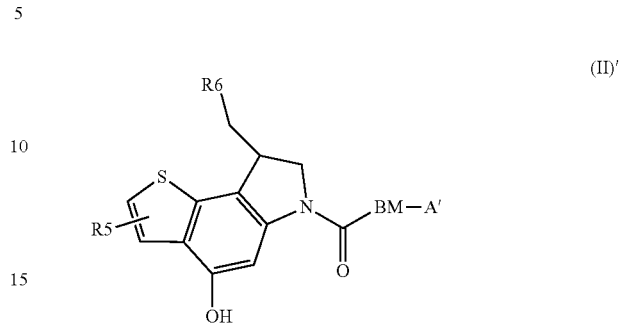

(II)' wherein A' is null,
R4 and R6 are as defined above and
BM is a binding moiety of formula (V) as defined above, with a compound of formula (XX)'

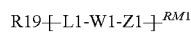

(XX)' wherein L1 is as defined above but not hydrogen and R19, W1, Z1 and RM1 are as defined above, to give a compound of formula (IV)'''

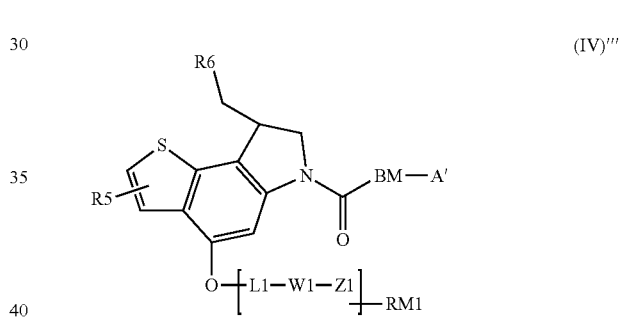

(IV)''' wherein A' is null,
L1 is as defined above except hydrogen,
R5, R6 and BM are as defined above, and
W1, Z1 and RM1 are as defined above and at least one of them is not null,
and the pharmaceutically acceptable salts thereof.

Accordingly, the preparation of a compound of formula (IV), wherein A' is null, is depicted in Scheme 4 below:

Scheme 4

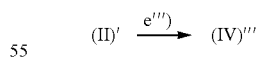

According to step e''') the coupling is performed as described under e") above.

From all of the above, it is clear to the skilled person that when preparing the compounds of formula (I), (II), (III) and (IV) according to any one of the aforementioned process variants, optional functional groups within the starting materials or the intermediates thereof that could give rise to unwanted side reactions need to be properly protected according to conventional techniques. Likewise, the conversion of these latter into the free deprotected compounds may be carried out according to known procedures.

As it will be readily appreciated, if the compounds of formula (I), (II), (III) and (IV) prepared according to the process described above are obtained as mixture of isomers, their separation using conventional techniques into the single isomers of formula (I), (II), (III) and (IV) is within the scope of the present invention.

Preferably a compound of formula (II) wherein L1 is as defined above except hydrogen or a compound of formula (IV) wherein RM and/or RM1 are not null, and R5, R6, BM, A', L, W, Z, L1, W1 and Z1 are as defined above, is reacted:

g) with a compound of formula (XXII)

R17-RM (XXII)

wherein R17 is as defined above and RM is as defined above but not null, to give the corresponding compound of formula (IV) wherein RM is as defined above but not null, then optionally h) with a compound of formula (XXII)'

R17-RM1 (XXII)' wherein R17 is as defined above, and RM1 is as defined above but not null, to give the corresponding compound of formula (IV) wherein RM1 is as defined above but not null.

It is important to underline that the steps described under g) and h) may optionally occurs in reverse order, i.e. step h) first and then step g).

According to step g) and h) the coupling is performed as described under b) above.

Compounds of formula (XXII) and (XXII)' are commercially available or are known compounds or can be prepared by methods known to the expert in the art or as reported in Anticancer Agents in Med Chem 2008, (8) page 618-637 or in WO2010/009124.

Compound of formula (XXI) can be prepared accordingly one of the steps i), k), l), m), o) or p).

Preferably a compound of formula (XIX), wherein A' is —OH and BM is as defined above, is reacted:

i) with a compound of formula (XX)

R19—L-W—Z—RM (XX)

wherein R19 is null,
L is a group of formula (Xf')

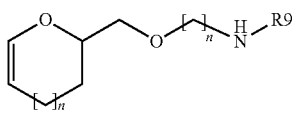

(Xf')

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;
n is as defined above and
W, Z and RM are null
or
R9 is null and
at least one of W, Z or RM is not null,
to give a compound of formula (XXI)

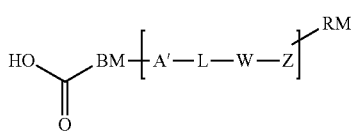

(XXI)

wherein A' is —O—, L is a group of formula (Xf), W, Z and RM are as defined above and BM is a group of formula (V)';
or
k) with a compound of formula (XX)

R19—L-W—Z—RM (XX)

wherein R19 is an activating —NH— group, preferably tosyl,
L is a group of formula —NHCOR9 (Xa), —NHCOO—R9 (Xc), or —NH—R9 (Xd);
wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
R9 is null and
at least one of W, Z or RM is not null,
to give a compound of formula (XXI)

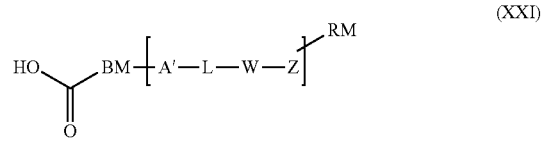

(XXI)

wherein A' is —O—, L is a group of formula (Xa), (Xc), (Xd) and BM, W, Z and RM are as defined above;
or
l) with a compound of formula of formula (XX)

R19—L-W—Z—RM (XX)

wherein R19 is R17 wherein R17 is —OH,
L is a group of formula (Xe)

(Xe)

wherein R9 and R10 are, each independently, hydrogen or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and W, Z and RM are null
or
one of R9 or R10 is null and at least one of W, Z or RM is not null,
to give a compound of formula (XXI)

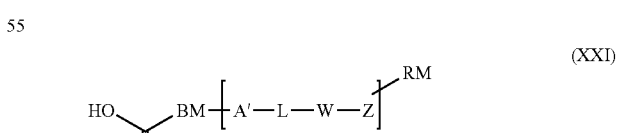

(XXI)

wherein A' is —O—, L is a group of formula (Xe) and BM, W, Z and RM are as defined above.

According to step i) the reaction is carried in an organic solvent, preferably DCM or DMF, in presence of PTSA at a temperature ranging from 20° C. to reflux and for a time ranging from 30 minutes to about 24 hours. Removal of the protecting group is performed using known procedure reported in the literature (see e.g. Protective Groups in Organic Synthesis; Theodora W. Greeen, Peter G. M. Wuts).

According to step k) the reaction is performed in a organic solvent, preferably ether, dioxane or a mixture of them with LiHMDS at a temperature ranging from −10° C. to 50° C. and for a time ranging from 30 minutes to about 24 hours. Removal of the protecting group is performed using known procedure reported in the literature (see e.g. Protective Groups in Organic Synthesis; Theodora W. Greeen, Peter G. M. Wuts).

According to step l) the reaction is performed in an organic solvent, preferably DCM, THF, $CH_3CN$ or $CCl_4$, optionally in presence of a base, preferably DIPEA, at a temperature ranging from −10° C. to 50° C. and for a time ranging from 30 minutes to about 24 hours.

Preferably a compound of formula (XIX) wherein A' is —OH or —$NH_2$ and BM is as defined above, is reacted:

m) with a compound of formula (XX)

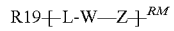  (XX)

wherein R19 is R17 wherein R17 is an activating moiety of the carboxylic group, preferably pyrrolidin-2,5-dione-1yl, L is a group of formula (Xj) or (Xk)

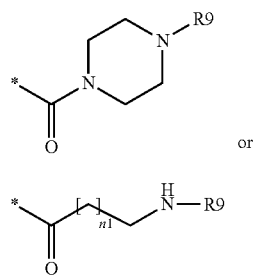

wherein R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl and
W, Z and RM are null
or
R9 is null and at least one of W, Z or RM is not null, to give a compound of formula (XXI)

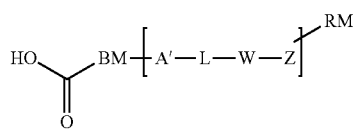

wherein A' is —O— or —NH, L is a group of formula (Xj) or (Xk) and BM, W, Z and RM are as defined above.

According to step m) the coupling reaction is performed in a organic solvent, preferably DCM, in basic conditions, e.g. TEA, DMAP. The reaction is carried out at a temperature ranging from 0° C. to reflux and for a time ranging from 30 minutes to about 24 hours.

Preferably a compound of formula (XIX) wherein A' is —COOH, and BM is as defined above, is reacted:
o) with a compound of formula (XX)

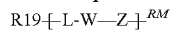  (XX)

wherein L is null,

W is a group of formula (XIa), (XIc), (XId), (XIk) and (XIj)

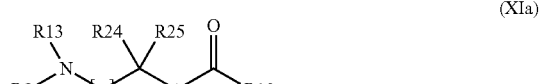

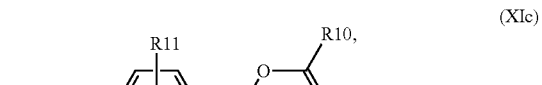

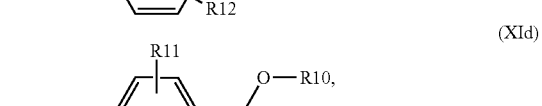

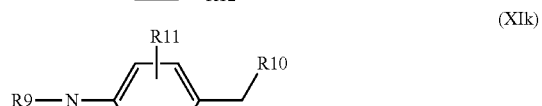

and

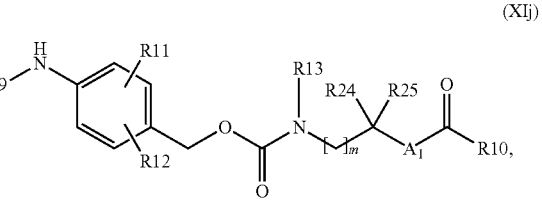

wherein R9 is hydrogen,
R10 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl,
R24, R25, R13, m and $A_1$ are as defined above and W, Z and RM are null
or
R10 is null, at least one of W, Z or RM is not null, and R24, R25, R13, m and $A_1$ are as defined above, to give a compound of formula (XXI)

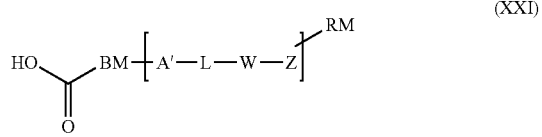

wherein A' is —CO—, L is null, W is a group of formula (XIa), (XIc), (XId), (XIk) and (XIj), BM, W, Z and RM are as defined above.

According to step o) the coupling reaction is performed using conditions well known in the literature (see e.g. Scott, C. J. et al. J. Med. Chem. 2005, 48, 1344-1358; Amino Acids, Peptides and Proteins in Organic Chemistry: Building Blocks, Catalysis and Coupling Chemistry, Volume 3; Andrew B. Hughes, Ayman El-Faham, Fernando Albericio).

Preferably a compound of formula (XIX) wherein A' is —OH or —$NH_2$, and BM is as defined above, is reacted:
p) with a compound of formula (XX)

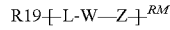  (XX)

wherein R19 is null, L is null, and W is a group of formula (XIa), (XIc), (XIk) (XIj) and (XIf)

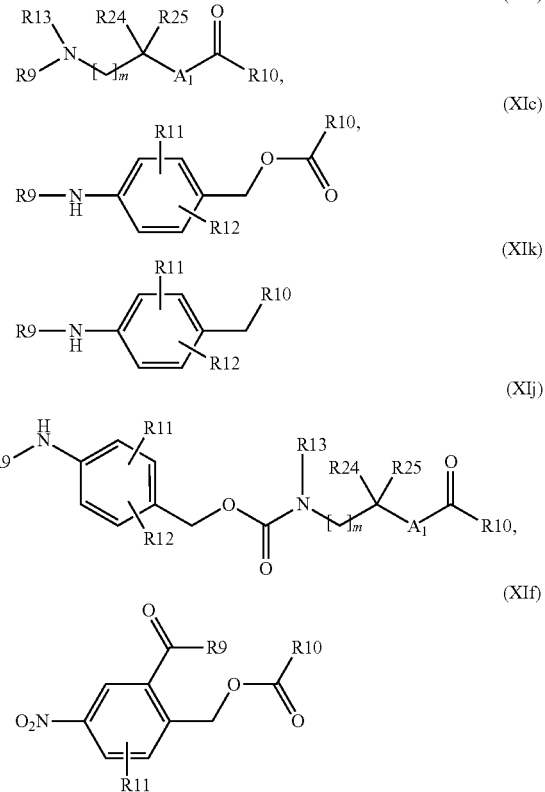

wherein R10 is —OH,

R9 is hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl, R24, R25, R13, m and $A_1$ are as defined above and W, Z and RM are null or R9 is null, at least one of W, Z or RM is not null, and R24, R25, R13, m and $A_1$ are as defined above, to give a compound of formula (XXI)

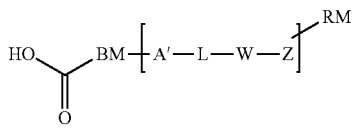

wherein A' is —O— or —NH—, L is null, W is a group of formula (XIa), (XIc), (XIk), (XIj) and (XIf), BM, W, Z and RM are as defined above.

According to step p) the coupling reaction is performed as described under o) above or following similar procedure as those reported in *J.O.C.* 2002, 67, 1866-11872; *Bioorg. Med. Chem.* 1996, 4, 1379-1391.

Steps i) to m) and p) can also be used to convert compounds of formula (IV)' to compounds of formula (IV)" by reaction with compounds of formula (XX)' (step f) or to convert compounds of formula (XV) to compounds of formula (IV)''' by reaction with compounds of formula (XX)' (step e") or to convert compounds of formula (II)' to compounds of formula (II)" by reaction with compounds of formula (XVIII) (step c) or to convert compounds of formula (XV) to compounds of formula (IV)' by reaction with compounds of formula (XX) (step e') or to convert compounds of formula (IV)''' to compounds of formula (IV)" by reaction with compounds of formula (XX) (step f").

Pharmacology

The compounds of the present invention are useful as antitumor agents.

A mammal, e.g. a human or animal, may therefore be treated by a method comprising administering there to a pharmaceutically effective amount of a compound of formula (I), (II), (III) or (IV).

The condition of the human or animal may be ameliorated or improved in this way.

The evaluation of the cytotoxicity of the compounds of formula (I), (II), (III), or (IV) is assessed as described below.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly, 25 μL/well of reagent solution are added to each well and after 5 minutes shaking microplates are read by a luminometer. The luminescent signal is proportional to the number of cells present in culture.

Representative compounds of the invention of formula (I) or (II) were tested in the specific in vitro cell proliferation assay described above.

All the tested compounds have an $IC_{50}$ value<0.5 μM (<500 nM) in A2780 human ovarian cancer cells.

As can be appreciated by the skilled person, all these representative compounds are thus particularly advantageous in antitumor therapy.

Furthermore the functionalized compounds of formula (III) or (IV) of the present invention are suitable to be conjugated.

The ability of the functionalized derivatives of formula (III) or (IV) to be conjugated has been assessed by conjugating them with a nucleophilic group such as the SH group of the cysteine aminoacid.

Preparation of a Conjugate 2 nmol of cysteine (MW: 121 Da) have been reacted with 2 nmol of a functionalized compound of formula (IV), i.e. Compd. 5 (MW: 1221 Da).

The reaction was incubated for 1 hour at 21° C. in presence of Borate buffer 50 mM pH 8, DTPA 2 mM, NaCl 50 mM, obtaining conjugate A1 (m/z=1343 (MH+)), then was analyzed by HPLC ESI-MS using a reversed phase HPLC method (PLRP-S column 1000Å 8 μM 150×2.1 mm) on a 1100 Agilent HPLC instrument coupled with an Agilent 1946 single quadrupole mass spectrometry detector with an orthogonal ESI source.

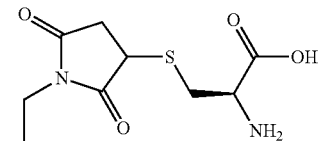
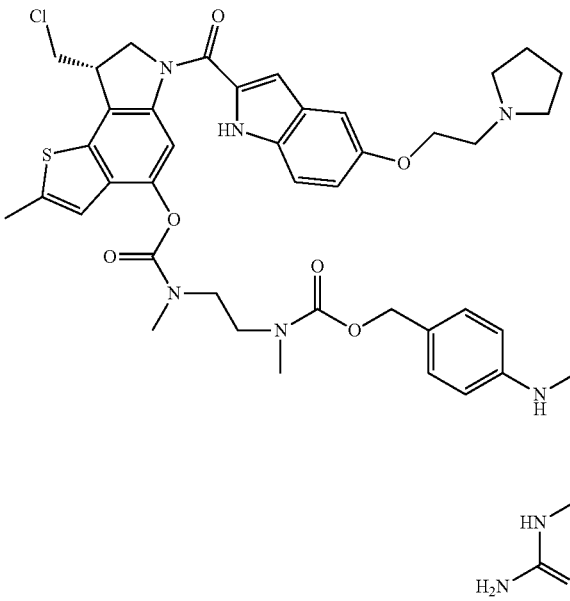

Conjugate A1
ESI MS: m/z = 1343 (MH+)

FIG. 1 shows the mass spectrum of the conjugate A1 and reports the molecular weight (m/z) on the x axis, while intensity expressed as counts per second (cps) is reported on the y axis.

Figure 2:
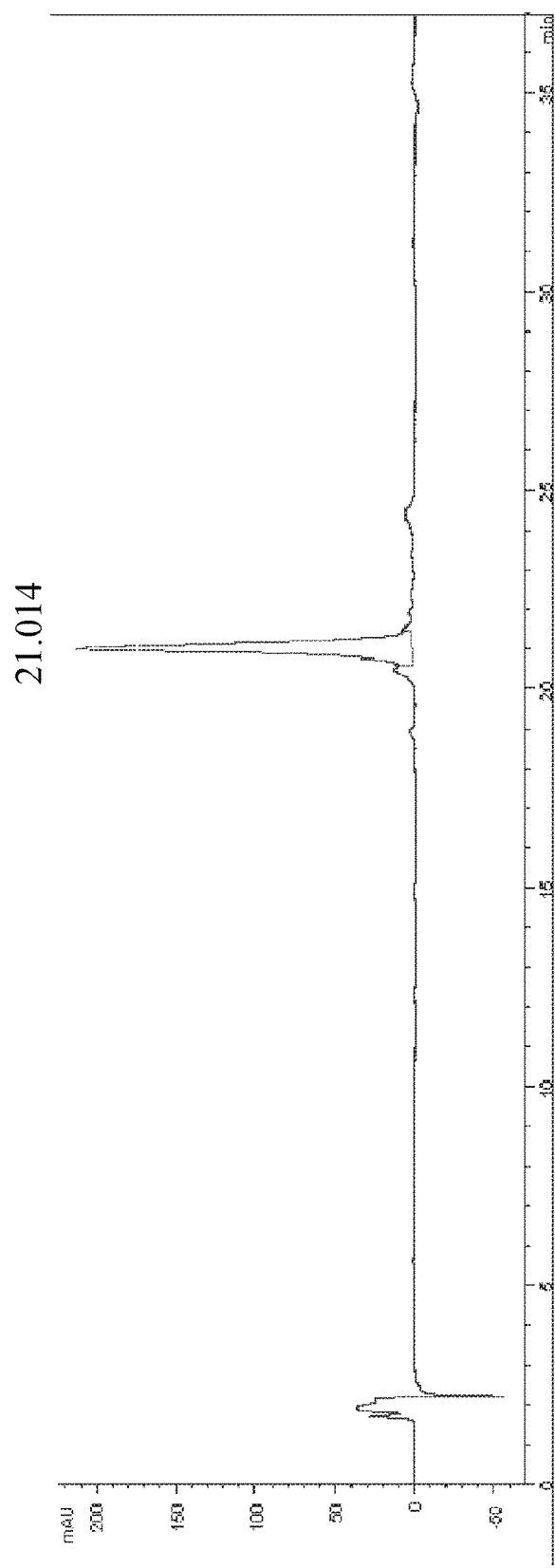
FIG. 2 is a display of a mass spectrum analysis shows the High-performance Liquid Chromatography (HPLC) profile of the conjugate A1, with the time (min) on the x axis, while UV absorbance (mAU) is reported on the y axis.

FIG. 2 shows the HPLC profile of the conjugate A1 and reports the time (min) on the x axis, while UV absorbance (mAU) is reported on the y axis.

Release of a Drug Moiety from a Conjugate

As an example, that is not intended to limit the scope of the invention, the release of a compound of formula (II) from the conjugate was performed in presence of cathepsin as reported below.

The conjugate A1 was incubated with 0.2 units of cathepsin B in sodium acetate buffer pH 5.5 and 1 mM Cys for 2 hours at 40° C.

Disappearance of the conjugate A1 and release of the corresponding compound of formula (II), i.e. compd. 1, as well as of its precursor A3, confirms the breaking of the Z peptidic linker of the conjugate.

Complete release of the compound of formula (II) from the conjugate has been observed by HPLC ESI-MS analysis.

Figure 3:
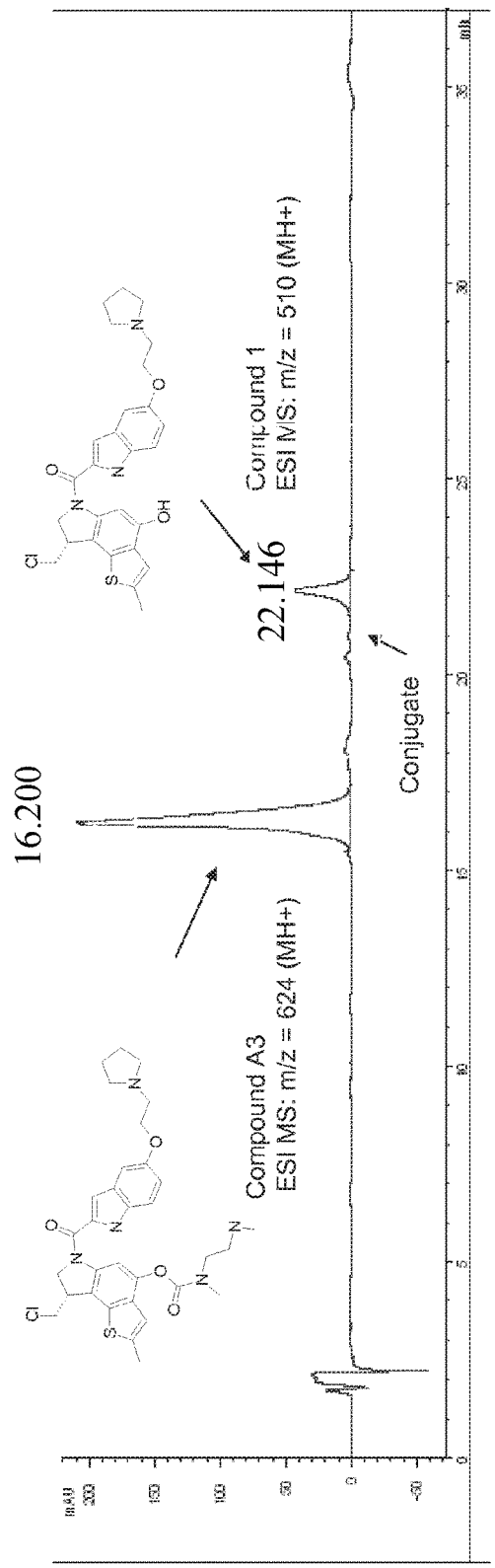
FIG. 3 is a display of HPLC analysis after 2 hours treatment of conjugate A1 with cathepsin, with the time (min) on the x axis, while UV absorbance (mAU) is reported on the y axis.

FIG. 3 shows the HPLC profile after 2 hours treatment of conjugate A1 with cathepsin and reports the time (min) on the x axis, while UV absorbance (mAU) is reported on the y axis.

Figure 4A:
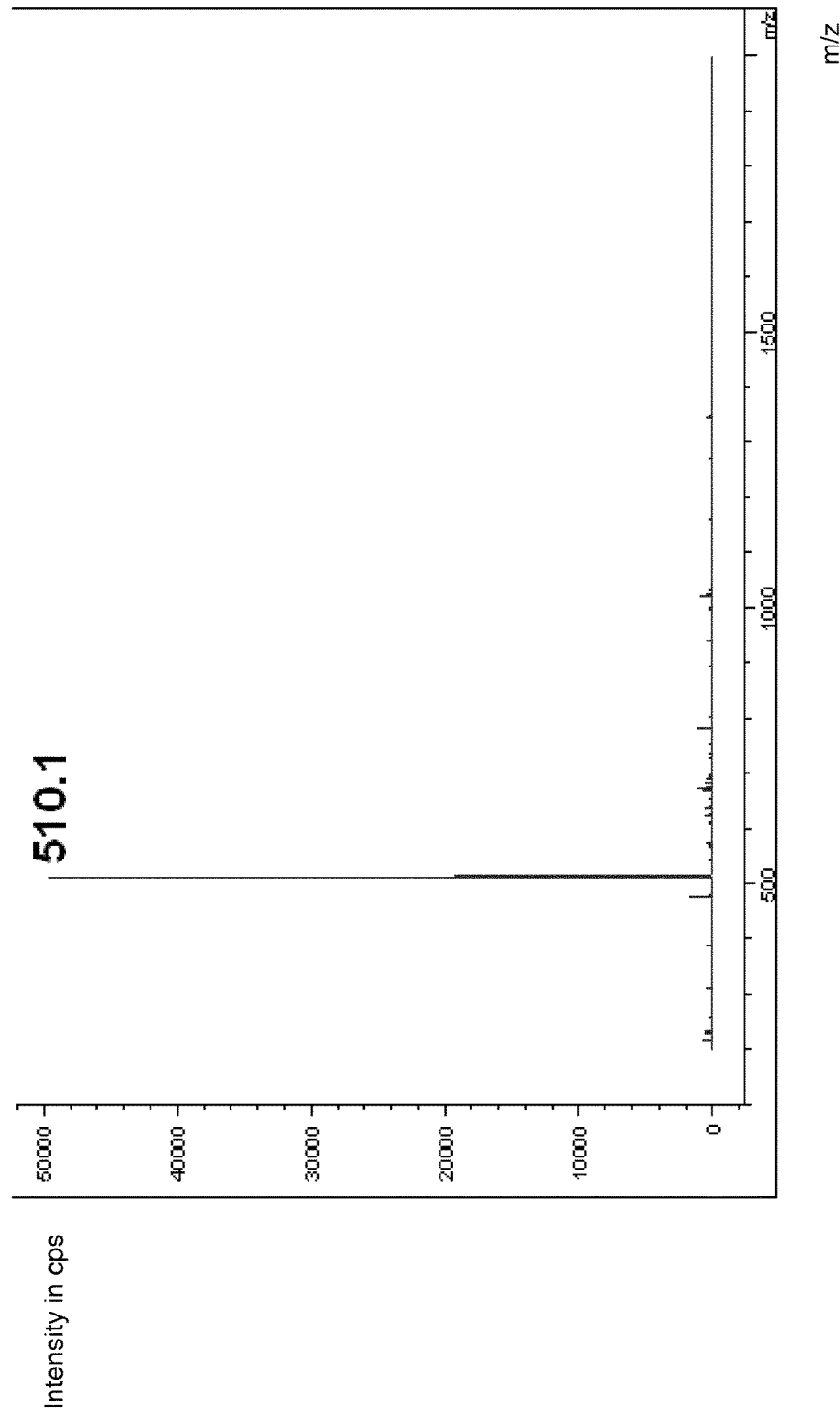
FIG. 4a is a display of the mass spectrum of the released Compd. 1, with the molecular weight (m/z) on the x axis, while intensity expressed as counts per second (cps) is reported on the y axis.

FIG. 4a shows the mass spectrum of the released Compd. 1 and reports the molecular weight (m/z) on the x axis, while intensity expressed as counts per second (cps) is reported on the y axis.

Figure 4B:
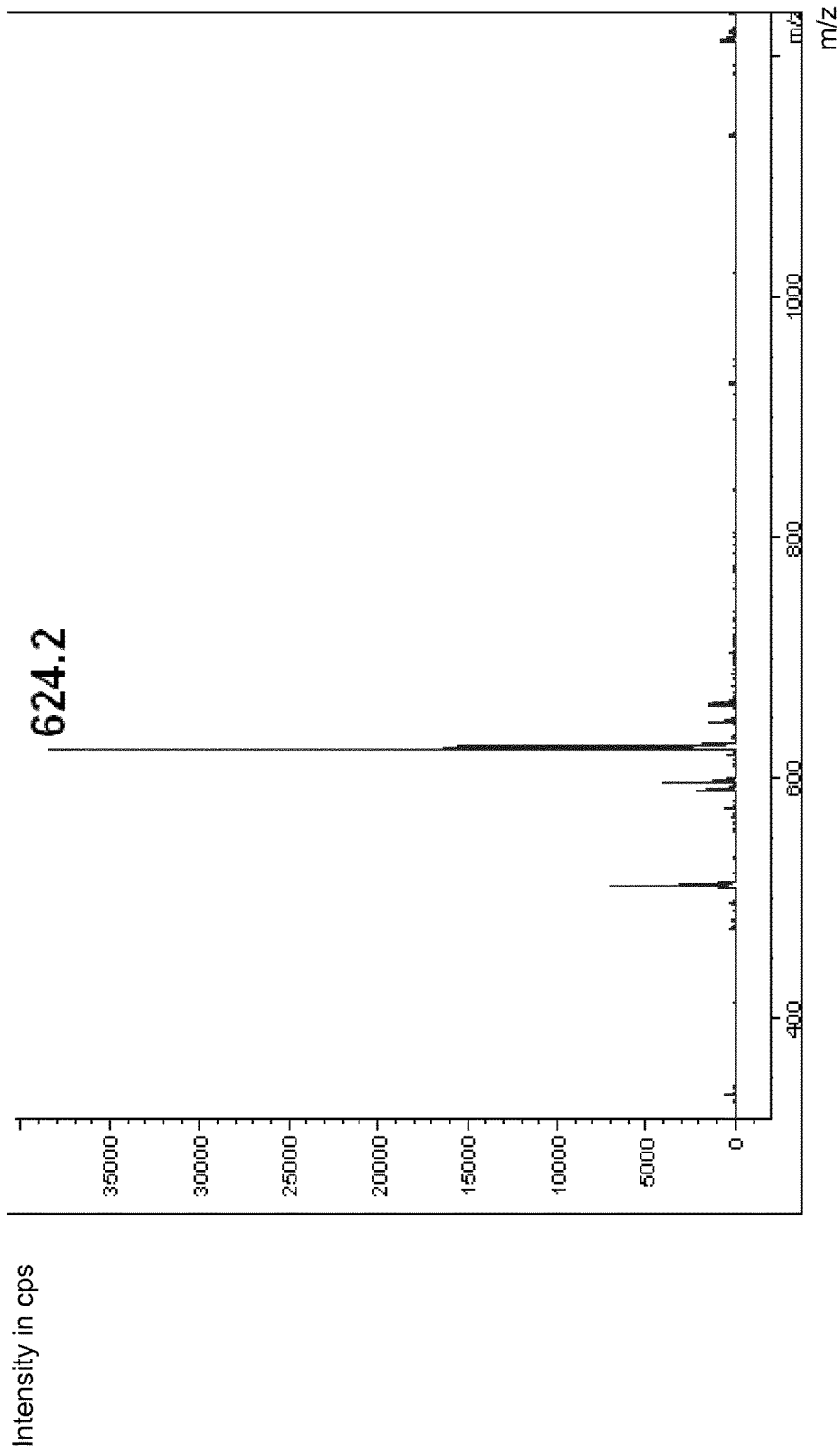
FIG. 4b is a display of the mass spectrum of the released Compound A3, with the molecular weight (m/z) on the x axis, while intensity expressed as counts per second (cps) is reported on the y axis.

FIG. 4b shows the mass spectrum of the released Compound A3, a precursor of compd. 1, and reports the molecular weight (m/z) on the x axis, while intensity expressed as counts per second (cps) is reported on the y axis.

The compounds of the present invention can be administered either as single agents or, alternatively, in combination with known anticancer treatments such as radiation therapy or chemotherapy regimen, in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I), (II), (III) or (IV) may be used sequentially with known anticancer agents when a combination formulation is inappropriate.

The compounds of formula (I), (II), (III) or (IV) of the present invention, suitable for administration to a mammal, e.g., to humans, can be administered by the usual routes and the dosage level depending upon the age, the weight, the conditions of the patient and the administration route.

For example, a suitable dosage adopted for oral administration of a compound of formula (I) may range from about 1 to about 300 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., subcutaneously, intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples.

The compounds of the present invention, as prepared according to the following examples, were also characterized by $^1$H-NMR and/or by Exact Mass data ESI(+).

$^1$H-NMR spectra were recorded at a constant temperature of 25° C. on a Varian INOVA 500 spectrometer (operating at 499.8 MHz for $^1$H) and equipped with 5 mm $^1$H z axis PFG Indirect Detection Cold-Probe or alternatively with 5 mm $^1$H z axis PFG Triple Resonance Probe.

Chemical shifts were referenced with respect to the residual solvents signals. Data are reported as follows: chemical shift (δ), multiplicity (s=singlet, d=doublet, t=triplet, q=quartet, br. s=broad singlet, td=triplet of doublet, dd=doublet of doublets, ddd=doublet of doublets of doublets, m=multiplet), coupling constants (Hz), and number of protons.

Exact Mass data ESI(+) were obtained on a Waters Q-Tof Ultima mass spectrometer directly connected with a Agilent 1100 micro-HPLC system as previously described (M. Colombo, F. Riccardi-Sirtori, V. Rizzo, Rapid Commun. Mass Spectrom. 2004, 18, 511-517).

In the examples below as well as throughout the application, the following abbreviations have the following meanings. If not defined, the terms have their generally accepted meanings.

| | ABBREVIATIONS |
|---|---|
| DCC | N,N'-dicyclohexylcarbodiimide |
| DBU | diazabicycloundecene |
| DCM | dichloromethane |
| DIPEA | N,N-diisopropyethylamine |
| DMAP | N,N-dimethylaminopyridine |
| DMF | N,N-dimethylformamide |
| DMSO | dimethyl sulfoxide |
| EDCl | N-ethyl-N',N'-diisopropyl carbodiimide hydrochloride |
| EDC | 1-ethyl-3-(3-dimethylaminopropyl)carbodiimide |
| Et$_2$O | diethyl ether |
| EtOAc | ethyl acetate |
| EtOH | ethanol |
| HCl | hydrochloric acid |
| HOBt | 1H-benzotriazol-1-ol |
| LiHMDS | lithium bis(trimethylsilyl)amide |
| MeOH | methanol |
| Na$_2$SO$_4$ | sodium sulfate |
| NaHCO$_3$ | sodium hydrogen carbonate |
| NaOH | sodium hydroxide |
| TEA | triethylamine |
| TFA | trifluoro acetic acid |
| THF | tetrahydrofurane |

Example 1

Step b, Step e'''

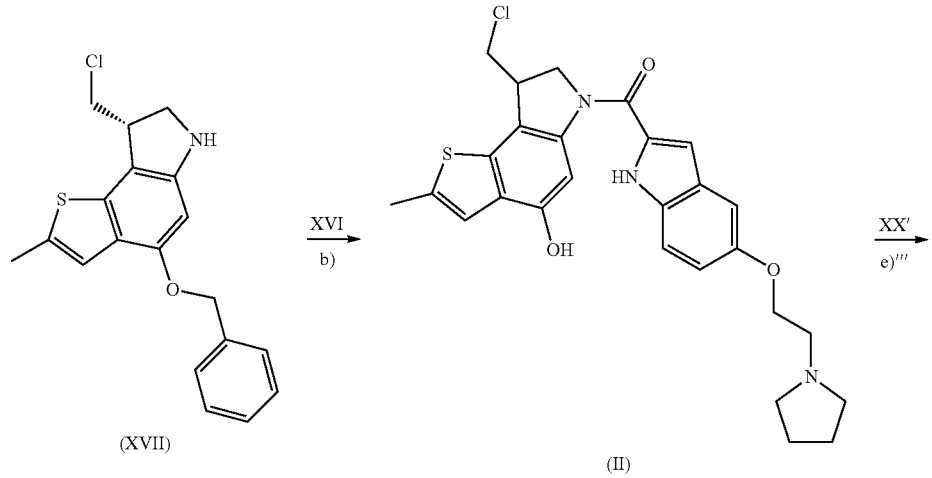

-continued

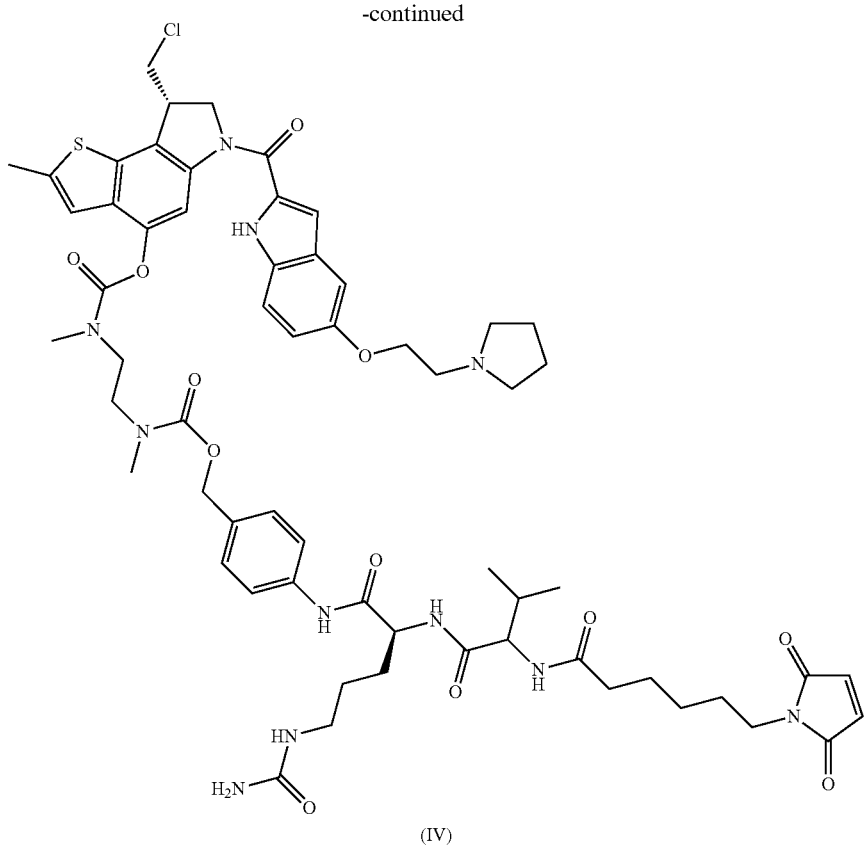

(IV)

N-[6-(2,5-dioxo-2,5-dihydro-1H-pyrrol-1-yl)hexanoyl]-L-valyl-N5-carbamoyl-N-[4-({[{2-[({[(8S)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide (Comp. 5)

Step b

To (8S)-4-(benzyloxy)-8-(chloromethyl)-2-methyl-7,8-dihydro-6H-thieno[2,3-e]indole (19.2 mg, 0.056 mmol) (prepared as reported in *J. Am. Chem. Soc.* 2007, 129, 14092) dissolved in 2.5 mL of dry DMF, were added 5-[2-(pyrrolidin-1-yl)ethoxy]-1H-indole-2-carboxylic acid (26 mg, 0.095 mmol) and EDC HCl (43 mg, 0.22 mmol). The reaction mixture was stirred overnight under nitrogen atmosphere, diluted with EtOAc and washed with a saturated solution of Na$_2$CO$_3$ in water. Organic phase was dried over Na$_2$SO$_4$, filtered and evaporated to dryness. Crude product was purified by column chromatography (DCM/MeOH/NH$_3$ in MeOH=100/1/1) affording [(8S)-4-(benzyloxy)-8-(chloromethyl)-2-methyl-7,8-dihydro-6H-thieno[2,3-e]indol-6-yl]{5-[2-(pyrrolidin-1-yl)ethoxy]-1H-indol-2-yl}methanone (30 mg, 89% yield).

ESI MS: m/z 600 (MH+)

$^1$H NMR (500 MHz, acetone) δ 1.73 (m, 4 H), 2.52 (m, 7 H), 2.87 (t, J=5.8 Hz, 3 H), 4.00 (m, 1 H), 4.13 (m, 5 H), 4.67 (dd, J=10.8, 4.2 Hz, 1 H), 4.88 (m, 1 H), 5.27 (s, 2 H), 6.97 (dd, J=8.9, 2.5 Hz, 1 H), 7.13 (d, J=1.6 Hz, 1 H), 7.19 (d, J=2.33 Hz, 1 H), 7.20 (m, 1 H), 7.35 (m, 1 H), 7.42 (m, 2 H), 7.49 (d, J=8.9 Hz, 1 H), 7.57 (d, J=7.4 Hz, 2H), 8.14 (s, 1 H), 10.71 (br. s., 1 H)

Deprotection

[(8S)-8-(chloromethyl)-4-hydroxy-2-methyl-7,8-dihydro-6H-thieno[2,3-e]indol-6-yl]{5-[2-(pyrrolidin-1-yl)ethoxy]-1H-indol-2-yl}methanone (Comp. 1)

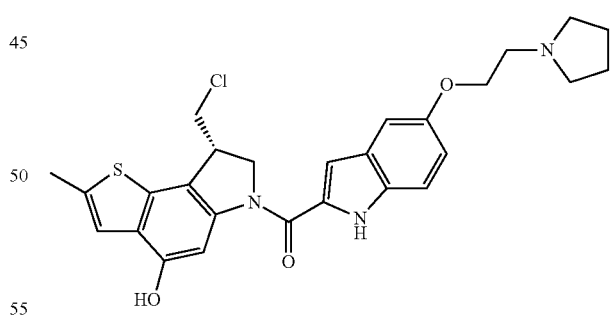

[(8S)-4-(benzyloxy)-8-(chloromethyl)-2-methyl-7,8-dihydro-6H-thieno[2,3-e]indol-6-yl]{5-[2-(pyrrolidin-1-yl)ethoxy]-1H-indol-2-yl}methanone (28 mg, 0.0466 mmol) was stirred in 2 mL of 3.5 M HCl in EtOAc for 1 hour and evaporated to dryness. The product was dissolved in THF (8 mL) and 25% aq. HCO$_2$NH$_4$ (0.175 mL) and 10% Pd—C (25 mg) were added. The resulting mixture was stirred at room temperature for 16 hours, filtered through Celite and concentrated to yield after chromatographic purification (DCM/MeOH/HCl conc 100/5/0.1) [(8S)-8-(chloromethyl)-4-hydroxy-2-methyl-7,8-dihydro-6H-thieno[2,3-e]indol-6- yl]{5-[2-(pyrrolidin-1-yl)ethoxy]-1H-indol-2-yl}methanone hydrochloride (13 mg, 51% yield).

ESI MS: m/z 510 (MH+)

$^1$H NMR (500 MHz, METHANOL-d$_4$) δ 2.10 (br. s., 4 H), 2.62 (s, 3 H), 3.32 (m, 2 H) 3.50 (m, 2 H), 3.70 (t, J=6.4 Hz, 1 H), 3.86 (dd, J=11.1, 7.8 Hz, 1 H), 4.03 (m, 1 H), 4.09 (dd, J=11.1, 3.4 Hz, 1 H), 4.36 (t, J=5.0 Hz, 2 H), 4.64 (dd, J=11.1, 3.4 Hz, 1 H), 4.80 (t, J=9.9 Hz, 1 H), 7.08 (dd, J=8.9, 2.6 Hz, 1 H), 7.13 (s, 1 H), 7.18 (m, 1 H), 7.30 (d, J=2.6 Hz, 1 H), 7.48 (d, J=8.9 Hz, 1 H), 7.76 (br. s., 1 H)

Analogously the Following Compounds have been Prepared

[(8R)-8-(chloromethyl)-4-hydroxy-2-methyl-7,8-dihydro-6H-thieno[2,3-e]indol-6-yl]{5-[2-(pyrrolidin-1-yl)ethoxy]-1H-indol-2-yl}methanone (Comp. 2)

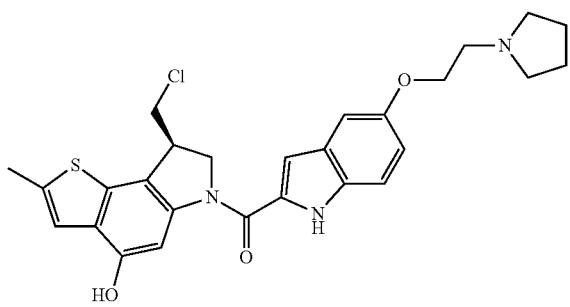 [SMILES: Cc1cc2c(O)cc3c(c2s1)[C@@H](CCl)CN3C(=O)c1cc2cc(OCCN3CCCC3)ccc2[nH]1]

ESI MS: m/z 510 (MH+)

Step e''' The Title Compound

A solution of [(8S)-8-(chloromethyl)-4-hydroxy-2-methyl-7,8-dihydro-6H-thieno[2,3-e]indol-6-yl]{5-[2-(pyrrolidin-1-yl)ethoxy]-1H-indol-2-yl}methanone hydrochloride (10 mg, 0.0183 mmol), 4-nitrophenyl carbonochloridate (22 mg, 0.11 mmol) and triethylamine (0.021 mL, 0.146 mmol) in 1 mL of dry DCM and 1 mL of dry THF was stirred under nitrogen atmosphere for 6 hours. Solvents were evaporated and the residue was treated with diethylether. The resulting precipitate was filtered, washed with diethylether and dried under vacuum. This compound was dissolved in dry DCM (2 mL, with 10% of dry DMF) and N-[6-(2,5-dioxo-2,5-dihydro-1H-pyrrol-1-yl)hexanoyl]-L-valyl-N$^5$-carbamoyl-N-{4-[({methyl[2-(methylamino)ethyl]carbamoyl}oxy)methyl]phenyl}-L-ornithinamide hydrochloride (XX)' (prepared as reported below) (30 mg, 0.04 mmol) and triethylamine (0.016 mL, 0.11 mmol) were added. The reaction mixture was stirred overnight under nitrogen atmosphere, solvents were evaporated and the title compound (8 mg, 36% yield) was obtained after column chromatography purification (DCM/MeOH=85/15).

ESI MS: m/z 1222 (MH+)

$^1$H NMR (500 MHz, METHANOL-d$_4$) δ 0.99 (m, 6 H), 1.24-1.90 (m, 10 H), 2.03 (m, 4 H), 2.07 (m, 1 H), 2.27 (m, 2 H), 2.54 (m, 3 H), 2.93-3.05 (m, 6 H), 3.13-3.42 (m, 2 H), 3.45 (m, 4 H), 3.64 (m, 2 H), 4.09 (m, 1 H), 4.15 (d, 1 H), 4.30 (m, 2 H), 4.47 (m, 1 H), 5.00-5.17 (m, 2 H), 6.77 (m, 2 H), 6.99-7.65 (m, 9 H), 7.99 (br. s., 1 H)

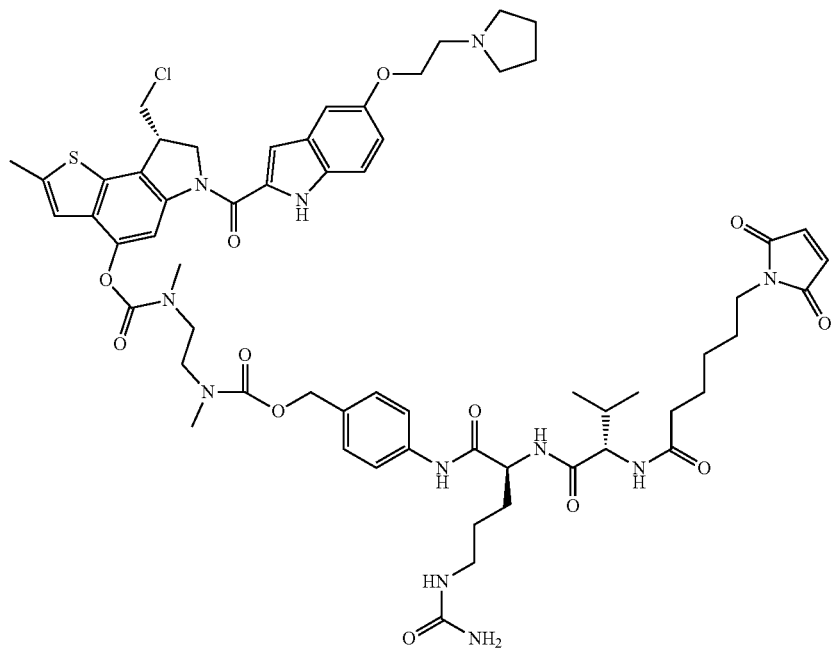 [SMILES: Cc1cc2c(OC(=O)N(C)CCN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c2s1)[C@H](CCl)CN3C(=O)c1cc2cc(OCCN3CCCC3)ccc2[nH]1]

Analogously the Following Compound has been Prepared

N-[6-(2,5-dioxo-2,5-dihydro-1H-pyrrol-1-yl)hexanoyl]-L-valyl-$N^5$-carbamoyl-N-[4-({[{2-[({[(8R)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide (Comp. 6)

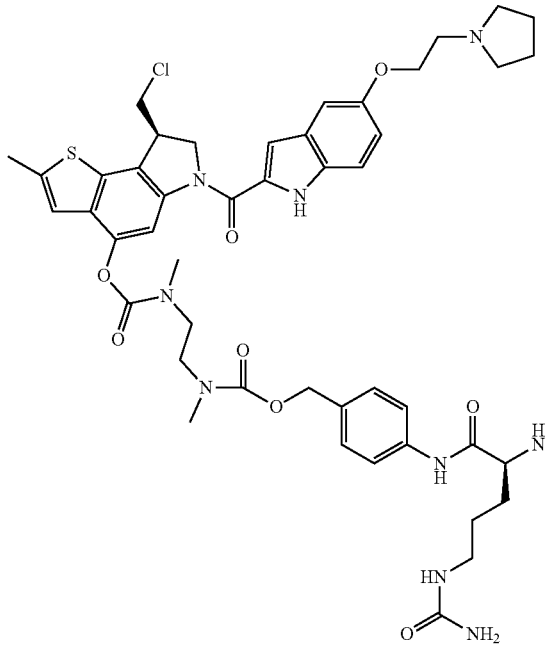

ESI MS: m/z 1222 (MH+)

Preparation of the Intermediate

N-[6-(2,5-dioxo-2,5-dihydro-1H-pyrrol-1-yl)hexanoyl]-L-valyl-$N^5$-carbamoyl-N-{4-[({methyl[2-(methylamino)ethyl]carbamoyl}oxy)methyl]phenyl}-L-ornithinamide hydrochloride (compound XX)'

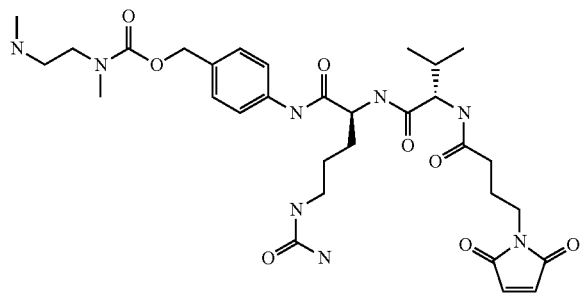 [SMILES: CNCCN(C)C(=O)OCc1ccc(NC(=O)[C@H](CCCNC(N)=O)NC(=O)[C@@H](NC(=O)CCCN2C(=O)C=CC2=O)C(C)C)cc1]

Step a

N-[(9H-fluoren-9-ylmethoxy)carbonyl]-L-valyl-$N^5$-carbamoyl-N-[4-(hydroxymethyl)phenyl]-L-ornithinamide (1.3 g, 2.16 mmol) (prepared as reported in EP0624377A2) and bis(4-nitrophenyl) carbonate (1.32 g, 4.34 mmol) were dissolved in 6 mL of dry DMF under nitrogen atmosphere, DIPEA (0.75 mL, 4.35 mmol) was added and the resulting solution was stirred an hour at room temperature. Diethylether (120 mL) was added, the resulting precipitate is filtered off, washed with diethylether and dried under vacuum affording N-[(9H-fluoren-9-ylmethoxy)carbonyl]-L-valyl-$N^5$-carbamoyl-N-[4-({[(4-nitrophenoxy)carbonyl]oxy}methyl)phenyl]-L-ornithinamide (1.47 g, 89% yield).

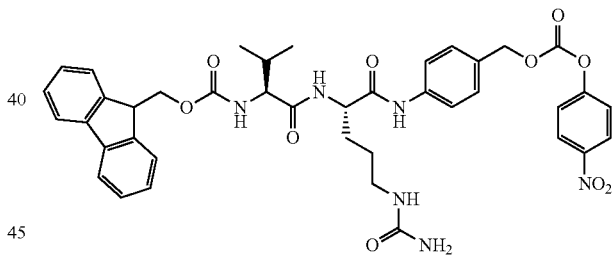

ESI MS: m/z 767 (MH+)

$^1$H NMR (400 MHz, DMSO-$d_6$) δ 0.86 (d, J=6.7 Hz, 3H), 0.88 (d, J=6.7 Hz, 3 H), 1.30-1.52 (m, 2 H), 1.60 (m, 1H), 1.69 (m, 1 H), 1.99 (m, 1 H), 2.90-3.10 (m, 2 H), 3.93 (dd, J=8.9, 7.0 Hz, 1 H), 4.14-4.34 (m, 3 H), 4.42 (m, 1 H), 5.24 (s, 2 H), 5.39 (s, 2 H), 5.97 (t, J=5.5 Hz, 1 H), 7.32 (m, 2 H), 7.42 (m, 5 H), 7.55 (m, 2 H), 7.65 (d, J=8.4 Hz, 2 H), 7.74 (t, J=7.9 Hz, 2 H), 7.88 (d, J=7.6 Hz, 2 H), 8.12 (d, J=7.4 Hz, 1 H), 8.31 (m, 2 H), 10.12 (s, 1 H)

Step b

N-[(9H-fluoren-9-ylmethoxy)carbonyl]-L-valyl-N-carbamoyl-N-[4-({[(4-nitrophenoxy)carbonyl]oxy}methyl)phenyl]-L-ornithinamide (310 mg, 0.404 mmol) and 2-(biphenyl-4-yl)propan-2-yl methyl[2-(methylamino)ethyl]carbamate (132 mg, 0.404 mmol) were dissolved in dry DMF (6 mL) and stirred under nitrogen atmosphere at room temperature for 3 hours. Solvent was evaporated and the resulting crude producy was purified by column chromatography (DCM/EtOH=9/1) affording N-[(9H-fluoren-9-ylmethoxy)carbonyl]-L-valyl-N-{4-[10-(biphenyl-4-yl)-4,7,10-trimethyl-3,8-dioxo-2,9-dioxa-4,7-diazaundec-1-yl]phenyl}-$N^5$-carbamoyl-L-ornithinamide (200 mg, 52% yield).

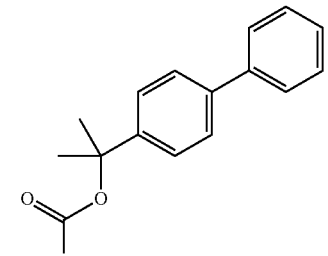
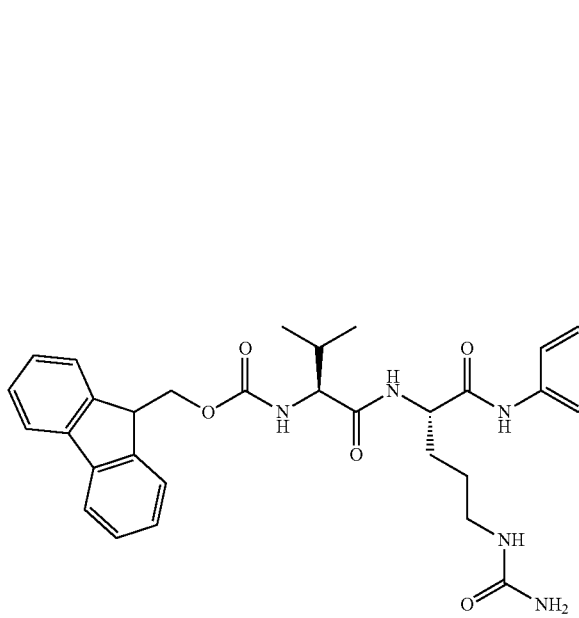

ESI MS: m/z 954 (MH+)

¹H NMR (500 MHz, DMSO-d₆) δ 0.86 (m, 6 H), 1.21-1.64 (m, 4H), 1.69 (s., 6 H), 2.00 (m, 1 H), 2.62-3.08 (m, 10 H), 3.44 (m, 2 H), 3.93 (t, J=7.6 Hz, 1 H), 4.22 (m, 1 H), 4.30 (m, 1 H), 4.42 (m, 1 H), 4.94-5.03 (m, 2 H), 5.39 (s, 2 H), 5.96 (m, 1 H), 7.25-7.46 (m, 11 H), 7.45-7.66 (m, 6 H), 7.74 (m, 2 H), 7.89 (m, 2 H), 8.11 (br. s., 1 H), 10.06 (br. s., 1 H)

Step c

To a solution of N-[(9H-fluoren-9-ylmethoxy)carbonyl]-L-valyl-N-{4-[10-(biphenyl-4-yl)-4,7,10-trimethyl-3,8-dioxo-2,9-dioxa-4,7-diazaundec-1-yl]phenyl}-N⁵-carbamoyl-L-ornithinamide (200 mg, 0.21 mmol) in dry DMF (6 mL) was added piperidine (0.105 mL, 1 mmol). The resulting solution was stirred at room temperature for 2 hours, concentrated to dryness to afford crude L-valyl-N-{4-[10-(biphenyl-4-yl)-4,7,10-trimethyl-3,8-dioxo-2,9-dioxa-4,7-diazaundec-1-yl]phenyl}-N⁵-carbamoyl-L-ornithinamide which was used without further purification. The crude intermediate was dissolved in dry DCM (6 mL) and 1-{6-[(2,5-dioxopyrrolidin-1-yl)oxy]-6-oxohexyl}-1H-pyrrole-2,5-dione (130 mg, 0.42 mmol) and triethylamine (0.088 mL, 0.63 mmol) were added. The resulting solution was stirred at room temperature overnight, solvents were evaporated and the residue was purified by column chromatography (DCM/EtOH=10/1) affording N-[(9H-fluoren-9-ylmethoxy)carbonyl]-L-valyl-N-{4-[10-(biphenyl-4-yl)-4,7,10-trimethyl-3,8-dioxo-2,9-dioxa-4,7-diazaundec-1-yl]phenyl}-N-carbamoyl-L-ornithinamide (150 mg, 77% yield).

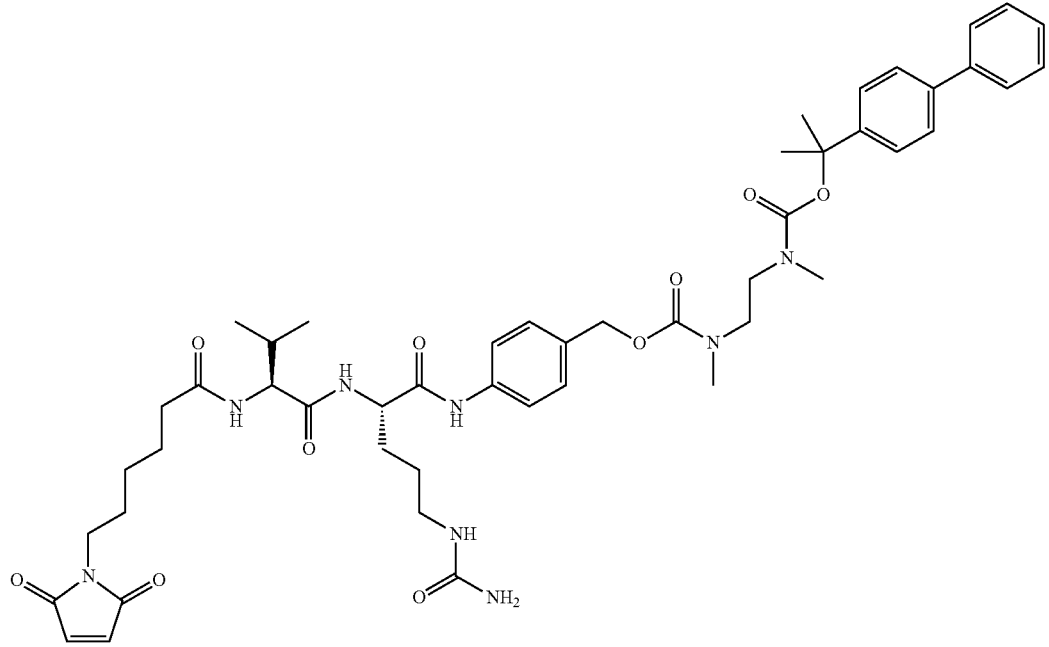 [SMILES: CC(C)[C@H](NC(=O)CCCCCN1C(=O)C=CC1=O)C(=O)N[C@@H](CCCNC(N)=O)C(=O)Nc1ccc(COC(=O)N(C)CCN(C)C(=O)OC(C)(C)c2ccc(-c3ccccc3)cc2)cc1]

ESI MS: m/z 925 (MH+)

$^1$H NMR (500 MHz, DMSO-$d_6$) δ 0.81 (d, J=6.7 Hz, 3 H), 0.84 (d, J=6.7 Hz, 3 H), 1.18 (m, 2 H), 1.36 (m, 1 H), 1.40-1.52 8 m, 6H), 1.60 (m, 1 H), 1.69 (s, 6 H), 1.97 (m, 1 H), 2.08-2.23 (m, 2 H), 2.63-2.96 (m, 8 H), 2.90 (m, 1 H), 3.01 (m, 1 H), 3.23-3.34 (m, 2H), 3.36 (m, 2H), 3.45 (m, 2 H), 4.19 (t, J=7.4 Hz, 1 H), 4.38 (m, 1 H), 4.95-5.05 (m, 2 H), 5.40 (s, 2 H), 5.97 (d, J=5.6 Hz, 1 H), 6.99 (s, 2 H), 7.25-7.41 (m, 5 H), 7.45 (m, 2 H), 7.53-7.66 (m, 6 H), 7.80 (d, J=9 Hz, 1 H), 8.08 (d, J=7.0 Hz, 1 H), 9.99 (m, 1 H), 10.76 (br. s., 1 H)

Step e The Tile Intermediate

N-[(9H-fluoren-9-ylmethoxy)carbonyl]-L-valyl-N-{4-[10-(biphenyl-4-yl)-4,7,10-trimethyl-3,8-dioxo-2,9-dioxa-4,7-diazaundec-1-yl]phenyl}-$N^5$-carbamoyl-L-ornithina-mide (50 mg, 0.054 mmol) was dissolved in 5 mL of dry THF and hydrochloric acid (4M in dioxane, 0.3 mL) was added. The solution was stirred for 3 minutes. The resulting precipitate was filtered off, washed with THF and dried under vacuum so affording the title compound (XX)' (36 mg, 92% yield).

ESI MS: m/z 687 (MH+)

$^1$H NMR (500 MHz, METHANOL-$d_4$) δ 0.97 (d, J=6.8, Hz, 3 H), 0.98 (d, J=6.8, Hz, 3 H), 1.31 (m, 2 H), 1.54-1.67 (m, 6 H), 1.76 (m, 1 H), 1.89 (m, 1 H), 2.08 (m, 1 H), 2.28 (t, J=7.5 Hz, 2 H), 2.64-2.75 (m, 3 H), 2.98 (s, 3 H), 3.11 (m, 1 H), 3.20 (m, 3 H), 3.48 (t, J=7.1 Hz, 2 H), 3.61 (t, J=5.7 Hz, 2 H), 4.14 (d, J=7.5, Hz 1 H), 4.50 (dd, J=9.1, 4.9 Hz, 1 H), 5.11 (s, 2 H), 6.79 (s, 2 H), 7.35 (d, J=8.3 Hz, 2 H), 7.60 (d, J=8.3 Hz, 2 H)

The invention claimed is:

1. A compound of formula (III) or (IV)

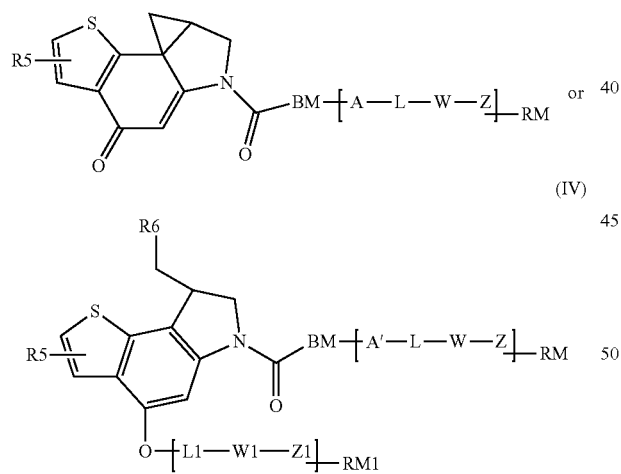

characterized in that

BM is a DNA binding moiety of formula (V)':

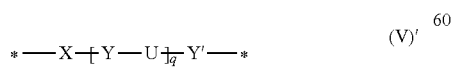

wherein:
X is null or linear or branched $C_2$-$C_4$ alkenyl;
Y and Y' are independently an optionally substituted aryl or heteroaryl;

U is a moiety of formula (VI) or (VII):

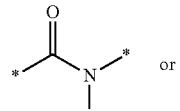

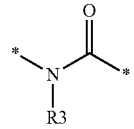

wherein R3 is hydrogen or a group selected from optionally substituted linear or branched $C_1$-$C_4$ alkyl and $C_1$-$C_4$ hydroxyalkyl; and
q is an integer from 0 to 3;
A is an atom selected from —O—, —NH— and —CO—;
A' is null or A;
L is null or a conditionally-cleavable moiety selected from;
—NHCO—R9(Xa); —NHCOO—R9(Xc); —NH—R9 (Xd);

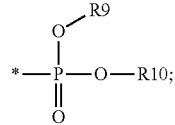

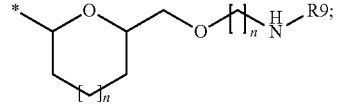

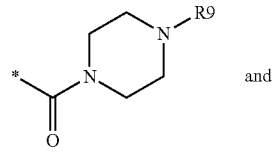

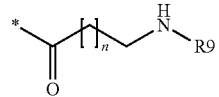

wherein:
R9 and R10 are, each independently, null, hydrogen, hydroxyl or an optionally substituted group selected from linear or branched $C_1$-$C_4$ alkyl, linear or branched $C_1$-$C_4$ hydroxyalkyl, linear or branched $C_1$-$C_4$ sulfhy-drylalkyl and linear or branched $C_1$-$C_4$ aminoalkyl;
each of n is independently an integer from 0 to 2 and n1 is an integer from 0 to 4;
W is null or a self-immolative system comprising one or more self-immolative groups independently selected from;

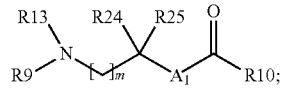

-continued

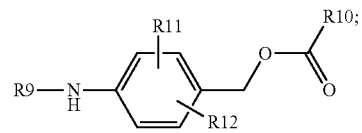
(XIc)

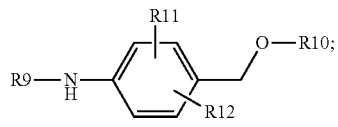
(XId)

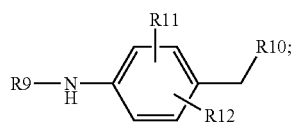
(XIk)

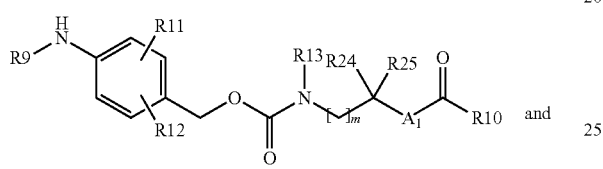
(XIj)

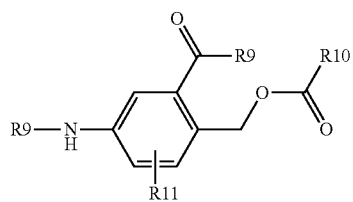
(XIf)

wherein
one of R9 and R10 is null and the other is null, hydrogen, hydroxyl or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;

R11 and R12 are, each independently, hydrogen, halogen, linear or branched $C_1$-$C_4$ alkyl or linear or branched $C_1$-$C_4$ hydroxyalkyl;

R24 and R25 are, each independently, hydrogen, halogen, methyl, ethyl, linear or branched $C_1$-$C_4$ hydroxyalkyl, linear or branched $C_1$-$C_4$ haloalkyl, or R24 and R25 taken together form a 3 to 6 membered carbocycle;

m is an integer from 0 to 3; and $A_1$ is $CH_2$, $CH_2N$—R13 or N—R13, wherein

R13 is hydrogen, linear or branched $C_1$-$C_4$ alkyl, linear or branched $C_1$-$C_4$ hydroxyalkyl or linear or branched $C_1$-$C_4$ haloalkyl;

Z is null or; a peptidic linker, a dipeptide linker, a tripeptide linker, or a non peptidic linker containing an oligoethylene glycol or polyethylene glycol moiety or a derivative thereof selected from:

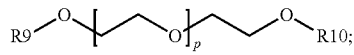
(XIIa)

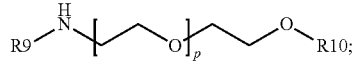
(XIIb)

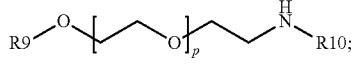
(XIId)

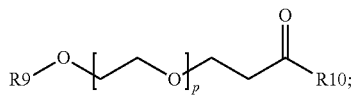
(XIIj)

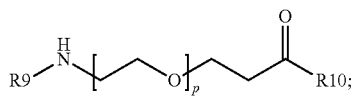
(XIIk)

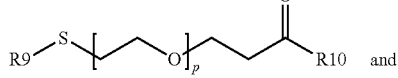
(XIIo)

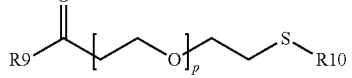
(XIIp)

wherein
one of R9 and R10 is null and the other is null, hydrogen, hydroxyl or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;

and p is an integer from 1 to 20;

RM is null or a reactive moiety selected from:

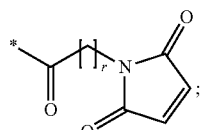
(XIIIa)

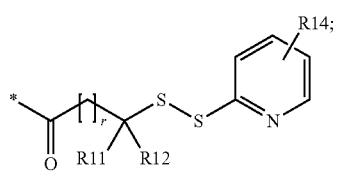
(XIIId)

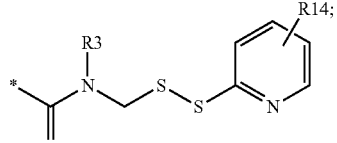
(XIIIg)

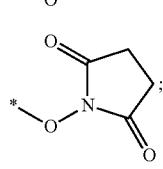
(XIIIh)

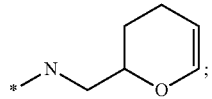
(XIIIi)

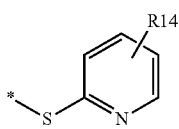 (XIIIj)

and

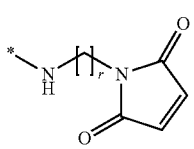 (XIIIm)

wherein R14 is $C_1$-$C_3$ alkyl or an electron-withdrawing group, preferably $NO_2$ and CN;
r is an integer from 0 to 7; and
R11 and R12 are, each independently, hydrogen, halogen, linear or branched $C_1$-$C_4$ alkyl or linear or branched $C_1$-$C_4$ hydroxyalkyl;
which is attached to at least one of the groups A, L, W or Z;
RM1 is null or RM attached to at least one of the groups selected from L1, W1 or Z1;
R5 is hydrogen, linear or branched $C_1$-$C_4$ alkyl, linear or branched $C_1$-$C_4$ hydroxyalkyl or linear or branched $C_1$-$C_4$ aminoalkyl;
R6 is halogen;
L1 is L;
W1 is null or a self-immolative system W;
Z1 is null or Z;
provided that:
in a compound of formula (III) at least one of L, W, Z or RM is not null; and
in a compound of formula (IV):
when L1 is hydrogen, then A' is not null and at least one of L, W, Z or RM is not null;
when A' is null, then L, W and Z are null and RM1 is not null;
and the pharmaceutically acceptable salts thereof.

2. A compound of formula (III) or (IV) according to claim 1, characterized in that R5 is linear or branched $C_1$-$C_4$ alkyl.

3. A compound of formula (IV) according to claim 2, characterized in that
A' is null and L1 is L, wherein L is null or a conditionally-cleavable moiety selected from:
—NHCO—R9(Xa); —NHCOO—R9(Xc); —NH—R9 (Xd);

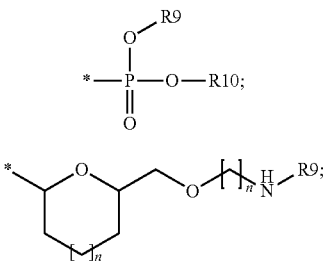 (Xe)

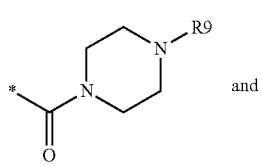 (Xf)

(Xj)

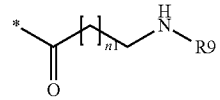 (Xk)

wherein:
R9 and R10 are, each independently, null, hydrogen, hydroxyl or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl;
each of n is independently an integer from 0 to 2 and n1 is an integer from 0 to 4.

4. A compound of formula (III) or (IV) according to claim 2, characterized in that
Z and Z1 are independently a peptidic linker, a dipeptide linker, a tripeptide linker, or a non peptidic linker containing an oligoethylene glycol or polyethylene glycol moiety or a derivative thereof selected from:

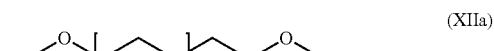 (XIIa)

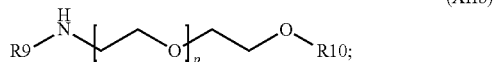 (XIIb)

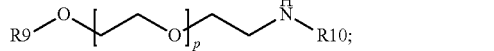 (XIId)

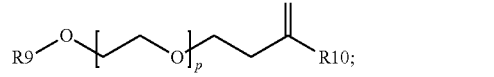 (XIIj)

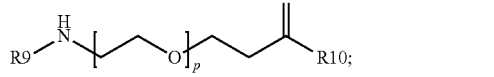 (XIIk)

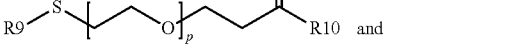 (XIIo)

and

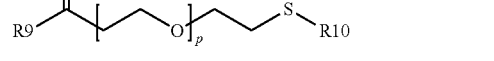 (XIIp)

wherein
one of R9 and R10 is null and the other is null, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl and linear or branched $C_1$-$C_4$ aminoalkyl; and
p is an integer from 1 to 20.

5. A compound according to claim 1, or a pharmaceutically acceptable salt thereof, which is selected from the group consisting of:
N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide and N-[6-(2,5-dioxo-2,5-dihydro-1H-pyrrol-1-yl)hexanoyl]-L-valyl-N$^5$-carbamoyl-N-[4-({[{2-[({[(8R)-8-(chloromethyl)-2-methyl-6-({5-[2-(pyrrolidin-1-yl)ethoxy]-1H-indol-2-yl}carbonyl)-7,8-dihydro-6H-thieno[2,3-e]indol-4-yl]oxy}carbonyl)(methyl)amino]ethyl}(methyl)carbamoyl]oxy}methyl)phenyl]-L-ornithinamide.

6. A pharmaceutical composition comprising a therapeutically effective amount of a compound of formula (III) or (IV), as defined in claim 1, and at least one pharmaceutically acceptable excipient, carrier or diluent.

7. A pharmaceutical composition according to claim 6 further comprising one or more chemotherapeutic agents.

8. A product comprising a compound of formula (III) or (IV), as defined in claim 1, or a pharmaceutically acceptable salt thereof and one or more chemotherapeutic agents, as a combined preparation for simultaneous, separate or sequential use in anticancer therapy.

9. A method of treating cancer, which comprises administering to a mammal in need thereof an effective amount of a compound of formula (III) or (IV), as defined in claim 1, wherein the cancer is selected from the group consisting of:
  carcinoma selected from teratocarcinoma or carcinoma of the bladder, breast, colon, kidney, liver, lung, esophagus, gallbladder, ovary, pancreas, stomach, cervix, thyroid, prostate or skin;
  leukaemia selected from acute lymphocytic leukaemia, acute lymphoblastic leukaemia, acute myelogenous leukaemia, chronic myelogenous leukaemia or promyelocytic leukaemia;
  lymphoma selected from B-cell lymphoma, T-cell lymphoma, Hodgkin's lymphoma, non-Hodgkin's lymphoma, hairy cell lymphoma or Burkitt's lymphoma;
  sarcoma selected from fibrosarcoma, rhabdomyosarcoma, osteosarcoma, or Kaposi's sarcoma;
  myelodysplastic syndrome, astrocytoma neuroblastoma, glioma, schwannomas, melanoma, seminoma, keratoxanthoma, thyroid follicular cancer and mesothelioma.

\* \* \* \* \*